United States Patent
Le Bihan et al.

(10) Patent No.: US 9,738,869 B2
(45) Date of Patent: Aug. 22, 2017

(54) METHOD AND SYSTEM FOR THE CULTURE OF MICROALGAE

(71) Applicants: CENTRE DE RECHERCHE INDUSTRIELLE DU QUEBEC, Québec (CA); INSTITUT NATIONAL D'OPTIQUE, Québec (CA)

(72) Inventors: Yann Le Bihan, Québec (CA); Marc Daigle, Québec (CA); Paul Grenier, Québec (CA); Marc Levesque, Saint-Augustin-de-Desmaures (CA)

(73) Assignees: CENTRE DE RECHERCHE INDUSTRIELLE DU QUEBEC, Quebec (CA); INSTITUT NATIONAL D'OPTIQUE, Quebec (CA)

( * ) Notice: Subject to any disclaimer, the term of this patent is extended or adjusted under 35 U.S.C. 154(b) by 0 days.

(21) Appl. No.: 14/289,277

(22) Filed: May 28, 2014

(65) Prior Publication Data
US 2014/0356931 A1    Dec. 4, 2014

Related U.S. Application Data

(60) Provisional application No. 61/828,226, filed on May 29, 2013.

(51) Int. Cl.
*C12N 1/12* (2006.01)
*C12M 1/00* (2006.01)
*C12M 1/34* (2006.01)
*C12N 1/02* (2006.01)

(52) U.S. Cl.
CPC .............. *C12N 1/12* (2013.01); *C12M 21/02* (2013.01); *C12M 23/18* (2013.01); *C12M 29/06* (2013.01); *C12M 31/08* (2013.01); *C12M 41/06* (2013.01); *C12M 41/42* (2013.01); *C12N 1/02* (2013.01)

(58) Field of Classification Search
None
See application file for complete search history.

(56) References Cited

U.S. PATENT DOCUMENTS

| | | | |
|---|---|---|---|
| 3,708,275 A * | 1/1973 | Camp, Jr. | C01B 25/301 423/309 |
| 3,958,364 A | 5/1976 | Schenck et al. | |
| 4,626,065 A * | 12/1986 | Mori | A01G 7/045 362/35 |
| 8,143,051 B2 | 3/2012 | Weissman et al. | |
| 8,183,032 B2 | 5/2012 | Frank | |
| 8,650,798 B1 * | 2/2014 | Armstrong | C12N 1/12 47/1.4 |
| 2009/0209014 A1 * | 8/2009 | Chi | C12P 7/6409 435/134 |
| 2009/0291485 A1 * | 11/2009 | Shigematsu | C12M 21/02 435/257.1 |
| 2009/0321349 A1 | 12/2009 | Offerman et al. | |
| 2010/0021968 A1 | 1/2010 | Hu et al. | |
| 2010/0120095 A1 | 5/2010 | Stroïazzo-Mougin et al. | |
| 2010/0139265 A1 | 6/2010 | Stroïazzo-Mougin | |
| 2010/0170149 A1 * | 7/2010 | Keeler | C12M 21/02 47/1.4 |
| 2010/0236137 A1 * | 9/2010 | Wu | A23K 1/009 44/385 |
| 2010/0255541 A1 | 10/2010 | Hu et al. | |
| 2010/0267122 A1 | 10/2010 | Chinnasamy et al. | |
| 2010/0330653 A1 * | 12/2010 | Hazlebeck | C12N 1/20 435/252.1 |
| 2011/0045528 A1 | 2/2011 | Dhamwichukorn | |
| 2011/0195085 A1 | 8/2011 | Kale | |
| 2011/0197317 A1 * | 8/2011 | Wong | A01G 7/02 800/296 |
| 2011/0269219 A1 | 11/2011 | Holland et al. | |
| 2011/0294196 A1 | 12/2011 | Machin | |
| 2012/0028338 A1 | 2/2012 | Bhatnagar et al. | |
| 2012/0034662 A1 | 2/2012 | Hu et al. | |
| 2012/0058542 A1 | 3/2012 | Wu et al. | |
| 2013/0029403 A1 * | 1/2013 | Hazlebeck | C12N 1/12 435/257.1 |
| 2013/0095544 A1 | 4/2013 | Berlowitz et al. | |
| 2013/0164322 A1 | 6/2013 | Durvasula et al. | |

FOREIGN PATENT DOCUMENTS

| | | |
|---|---|---|
| CN | 102399697 A | 4/2012 |
| CN | 102618446 A | 8/2012 |
| CN | 103571736 A | 2/2014 |
| FR | 2953856 A1 | 6/2011 |
| JP | 200060532 | 2/2000 |
| MY | 143383 A | 5/2011 |
| WO | 2013088407 A1 | 6/2013 |

OTHER PUBLICATIONS

Jiang, H et al. Effects of lowering temperature during culture on the production of polyunsaturated fatty acids in the marine diatom Phaeodactylum tricornutum (Bacillariophyceae). J. Phycol. 2004. 40: 651-654.*

(Continued)

*Primary Examiner* — Renee Claytor
*Assistant Examiner* — Susan E Fernandez
(74) *Attorney, Agent, or Firm* — Fasken Martineau DuMoulin, LLP

(57) ABSTRACT

Described is a method for the culture of microalgae, comprising: providing a consortium of at least two living species of microalgae; culturing under illumination the consortium in a controllable bioreactor and under non-sterile aqueous culture conditions; and controlling the culture conditions for affecting at least one of the following output: (i) flocculation and/or settling of said consortium of microalgae; and (ii) adhesion of the microalgae to surfaces of the bioreactor; wherein said culture conditions are controlled to promote (i) and/or to minimize (ii), without adversely affecting growth of the consortium of microalgae. It is also possible to control the culture conditions for affecting iii) the protein, carbohydrate, and/or fat content of the said microalgae consortium. A system for carrying out the method is also described.

27 Claims, 12 Drawing Sheets

(56) References Cited

OTHER PUBLICATIONS

Cadoret et al., "La production de biocarburant lipidique avec des microalgues : promesses et défis", Journal de la Société de Biologie, 2008, 35 pages, vol. 202 (3), France.

Chinnasamy et al., "Biomass and bioenergy production potential of microalgae consortium in open and closed bioreactors using untreated carpet industry effluent as growth medium", Bioresource Technology, 2010, pp. 6751-6760, vol. 101, Elsevier Ltd., USA.

Ian R. Davison, "Environmental effects on algal photosynthesis: Temperature", Journal of Phycology, 1991, pp. 2-8, vol. 27, University of Maine, Orono, USA.

Hauck et al., "Effects of simulated flue gas on growth of microalgae", Preprints of Papers, American Chemical Society, Division of Fuel Chemistry, Aug. 1996, pp. 1391-1396, vol. 41, Issue 4, Conference: 212, National meeting of the American Chemical Society, USA.

Jaouen et al., "The shear stress of microalgal cell suspensions", Bioresource Technology, 1999, pp. 149-154, vol. 68, Elsevier Ltd., USA.

Kumar et al., "Influence of nutrient loads, feeding frequency and inoculum source on growth of Chlorella vulgaris in digested piggery effluent culture medium", Bioresource technology, 2010, pp. 6012-6018, vol. 101, Elsevier Ltd., USA.

Lee et al., "Effects of SO2 and NO on growth of *Chlorella* sp. KR-1", Bioresource technology, 2002, pp. 1-4, vol. 82, Elsevier Ltd., USA.

Li Xin et al., "Effects of different nitrogen and phosphorus concentrations on the growth, nutrient uptake, and lipid accumulation of a freshwater microalgae *Scenedesmus* sp.", Bioresource technology, 2010, pp. 5494-5500, vol. 101, Elsevier Ltd., USA.

Mata et al., "Microalgae for biodiesel production and other applications: A review", Renewable and Sustainable Energy Reviews, 2010, pp. 217-232, vol. 14, Elsevier Ltd., USA.

Oilgae Report Academic Edition, Apr. 2011, 568 pages, Oilgae.com, India.

Olguin et al., "Population dynamics in mixed cultures of Neochloris oleoabundans and native microalgae from water of a polluted river and isolation of diatom consortium for the production of lipid rich biomass", New Biotechnology, Sep. 2013, pp. 705-715, vol. 30, No. 6, Elsevier b.v., USA.

Ono et al., "Selection of optimal microalgae species for CO2 sequestration", In Second National Conference on Carbon Sequestration, 2003, 7 pages, vol. 5. Available on the internet at http://www.alrc.doe.gov/publications/proceedings/03/carbon-seq/PDFs/158.pdf.

Sahoo et al., "Using algae for carbon dioxide capture and bio-fuel production to combat climate change", Phykos, 2012, pp. 32-38, vol. 42 (1), Phycological Society, India.

Salim et al., "Harvesting of microalgae by bio-flocculation", Journal of Applied Phycology, 2011, pp. 849-855, vol. 23, doi:10.1007/s10811-010-9591-x, Springer.

Shurin et al., "Traits diversity enhances yield in algal biofuel assemblages", Journal of Applied Ecology, 2014, 9 pages, doi:10.111/1365-2664.12242, British Ecological Society, UK.

Smith et al., "Applying ecological principles of crop cultivation in large-scale algal biomass production", Algal Research, 2013, 12 pages, htpp://dx.doi.org/10.1016/j.algal.2013.11.005, Elsevier Ltd., USA.

Tam et al., "Effect of ammonia concentrations on growth of Chlorella vulgaris and nitrogen removal from media", Bioresource Technology, 1996, pp. 45-50, vol. 57, Elsevier Ltd., USA.

Wilkie et al., "Indigenous algae for local bioresource production: Phycoprospecting", Energy for Sustainable Development, 2011, pp. 365-371, vol. 15, Elsevier Ltd., USA.

Yanagi et al., "CO2 fixation by *Chlorella* sp. HA-1 and its utilization", Energy Conversion and Management, 1995, pp. 713-716, vol. 36, No. 6-9, Elsevier Science Ltd., UK.

Chen et al., "Enhancing microalgal oil/lipid production from Chlorella sorokiniana CY1 using deep-sea water supplemented cultivation medium", Biochemical Engineering Journal, 2013, pp. 74-81, vol. 77, Elsevier Ltd., USA.

Da Rosa et al., "Carbon dioxide fixation by microalgae cultivated in open bioreactors", Energy Conversion and Management, 2011, pp. 3071-3073, vol. 52, Elsevier Ltd., USA.

Chinnasamy et al., "Microalgae cultivation in a wastewater dominated by carpet mill effluents for biofuel applications", Bioresource Technology, 2010, pp. 3097-3105, vol. 101, Elsevier Ltd., USA.

Mutanda et al., "Bioprospecting for hyper-lipid producing microalgal strains for sustainable biofuel production", Bioresource Technology, 2011, pp. 57-70, vol. 102, Elsevier Ltd., USA.

Chan et al., "Recycling of Nutrients from Trash Fish Wastewater for Microalgae Production as Health and Pharmaceutical Products and Renewable Energy", WebmedCentral Microbiology, 2011, 19 pages, 2(7): WMC002027, Downloaded from http://www.webmedcentral.com on Aug. 9, 2011.

Bing Hu, "Development of an effective swine manure-based algal cultivation system for biofuel & animal feed production and wastewater treatment", Dissertation submitter to the Faculty of University of Minnesota, Mar. 2013, 164 pages, USA.

Li et al., "Utilization of carbon dioxide from coal-fired power plant for the production of value-added products", Submitted in partial fulfillment of the requirements for the Design Engineering of Energy and Geo-Environmental Systems Course (EGEE 580), Apr. 2006, 109 pages, The Pennsylvania State University, USA.

Seambiotic Ltd., "Algae Pilot Plant Description Worksheet", 2010, 10 pages, Available on the internet at http://www.seambiotic.com/uploads/Seambiotic%20Ltd.%20-%20Algae%20Pilot%20Plant%20white%20paper.pdf, Israel.

SOLUTIONS4CO2, "Waste to high value omega-3 oils", Executive summary updated Jul. 2013, 2 pages, Toronto, Ontario.

Zhou et al., "Mass cultivation of microalgae on animal wastewater: A sequential two-stage cultivation process for energy crop and omega-3-rich animal feed production", Applied Biochemistry and Biotechnology, 2012, pp. 348-363, vol. 168, Springer.

Krustok et al., "Cultivation of indigenous algae for increased biogas production", International Conference on Applied Energy, Jul. 1-4, 2013, 7 pages, Paper ID: ICAE2013-123, South Africa.

Chen, High cell density culture of microalgae in heterotrophic growth, Trends in Biotechnology, Nov. 1996, p. 421-426, vol. 14, Issue 11, Elsevier Science Ltd.

Babel et al., Factors affecting seasonal variation of membrane filtration resistance caused by Chlorella algae, Water Research, 2002, pp. 1193-1292, vol. 36, Elsevier.

Di Pippo et al., Effect of light and temperature on biomass, photosynthesis and capsular polysaccharides in cultured phototrophic biofilms, Journal Appl Phycol, 2012, pp. 221-220, vol. 24, Springer.

How Fertilizer is made, Made How, 9 pages, vol. 3, Available on the internet at http://www.madehow.com/Volume-3/Fertilizer.html at least from Oct. 24, 2016.

Moheimani, Inorganic carbon and pH effect on growth and lipid productivity of Tetraselmis suecica and *Chlorella* sp (Chlorophyta) grown outdoors in bag photobioreactors, J Appl Phycol, 2013, pp. 387-398, vol. 25, Springer.

Tam et al., Effect of Ammonia Concentrations on Growth of Chlorella Vulgaris and Nitrogen Removal From Media, Bioresource Technoloy, 1996, pp. 45-50, vol. 57, Elsevier.

Wetherbee et al, The First Kiss: Establishment and Control of Initial Adhesion by Raphid Diatoms, J. Phycol. 1998, pp. 9-15, vol. 34.

Richmond, Handbook of Microalgal Culture, Biotechnology and Applied Phycology, 2004, p. 162, Blackwell.

Irving, Factors Influencing the Formation and Development of Microalgal Biofilms, 2010, 97 pages, Chemical Engineering and Applied Chemistry, University of Toronto.

\* cited by examiner

A                                B

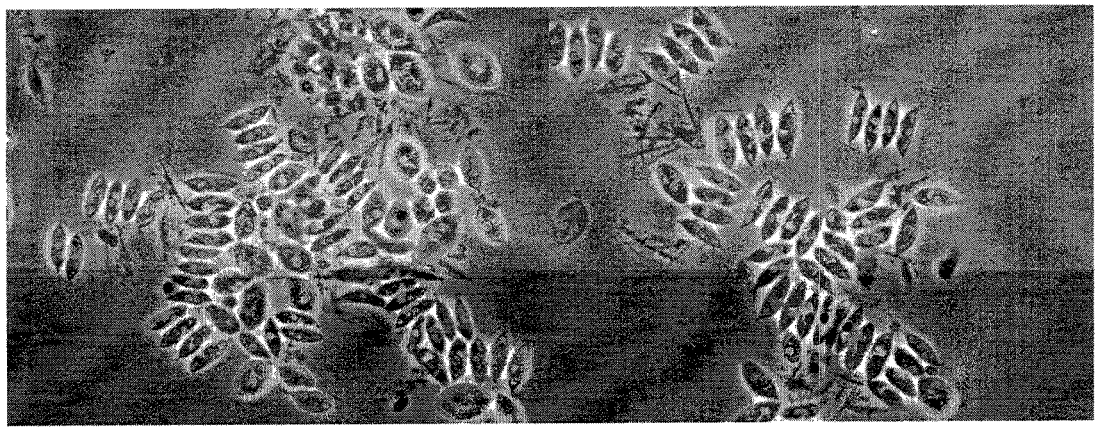
FIG. 15A　　　　　　　　　　　FIG. 15B
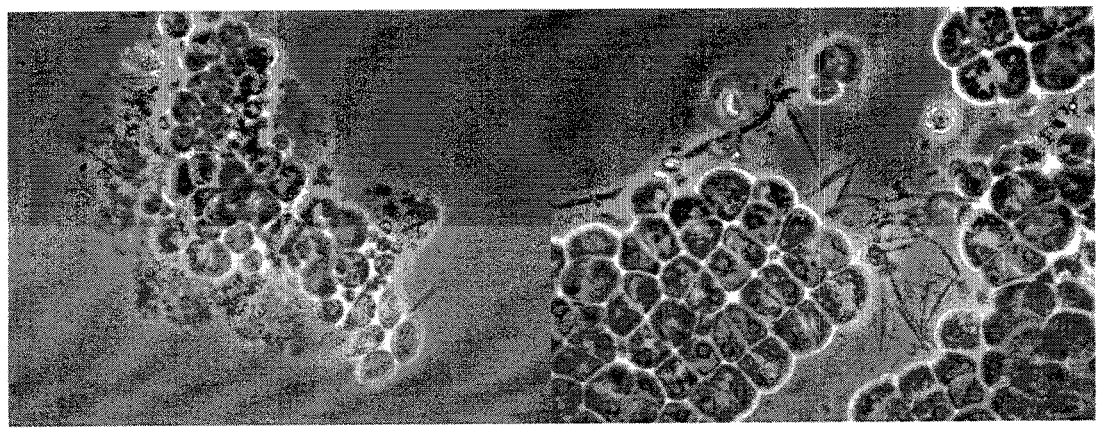
FIG. 15C　　　　　　　　　　　FIG. 15D
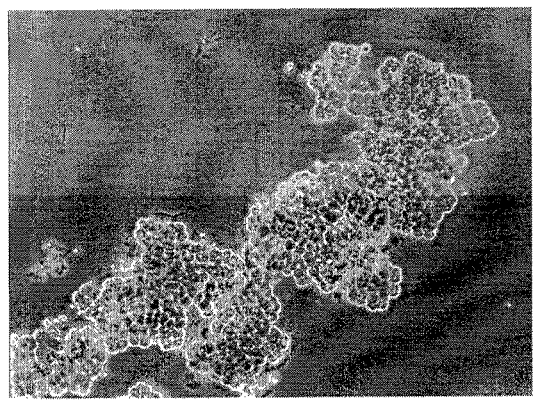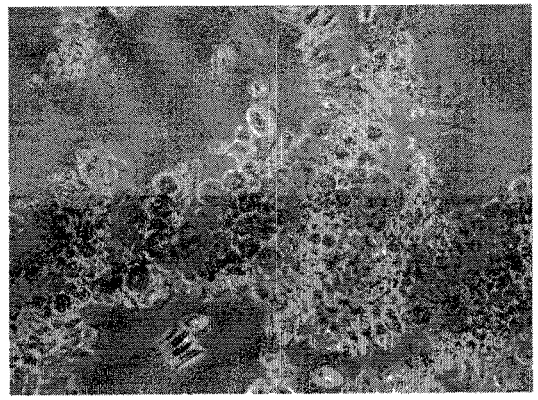
FIG. 15E　　　　　　　　　　　FIG. 15F

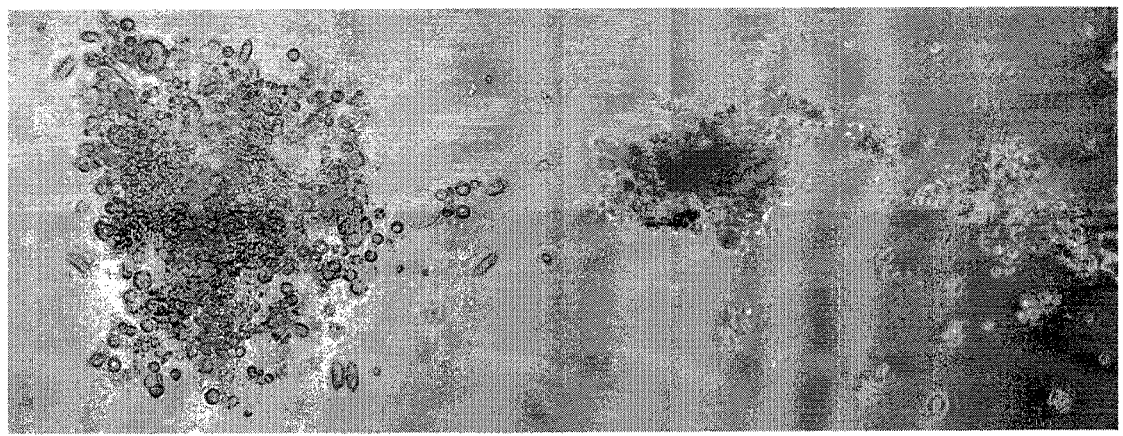
FIG. 15G                    FIG. 15H
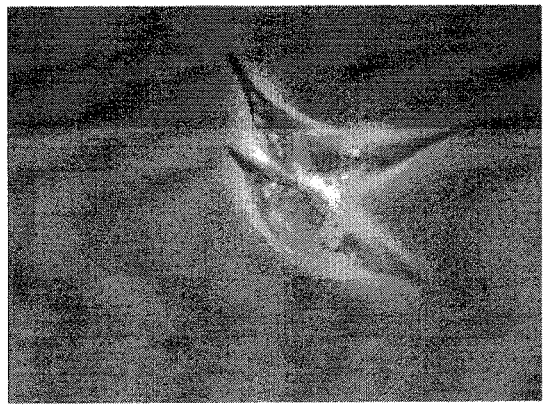 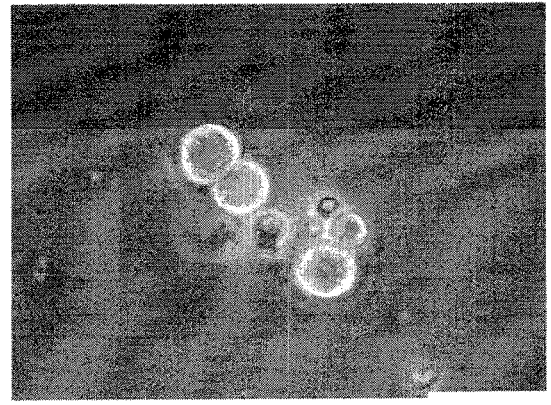
FIG. 15I                    FIG. 15J

METHOD AND SYSTEM FOR THE CULTURE OF MICROALGAE

TECHNICAL FIELD

The present invention pertains to the field of photosynthetic culture of microalgae. More particularly, the invention refers to methods, apparatus and systems for the growing of a consortium of microalgae in non-sterile culture conditions.

BACKGROUND OF THE ART

The photosynthetic culture of microalgae is becoming increasingly popular. This enthusiasm is due to the fact that the microalgae have an exceptional potential for the sequestration of $CO_2$, for the cleanup of wastes, the production of biofuels, and for the production of biosourced products such as pharmaceuticals and foodstuffs.

The approach most often used in the growing of microalgae consists in a monoculture, or the growing of a single species of algae. The monoculture systems generally operate under closed and sterile conditions and are complex, given that they require a close managing of several factors in order to prevent contamination by bacteria and pathogens, and also to ensure an adequate growth of the particular species of algae being grown. The selection of the appropriate type of algae placed in culture is generally critical, in order to maximize the yields associated with the specific use in mind (e.g., either the sequestration of $CO_2$, or the cleanup of wastes, or the production of biofuels, etc.). These culture systems may be also disadvantageous because they require the use of antibiotics or biocides to maintain the characteristics and the performance of the culture.

Some have suggested the possibility of growing indigenous algae for the purpose of boosting the production of biogas. Others have proposed the possibility of cultivating indigenous algae for the local production of biosourced products.

It has also been suggested to grow a consortium of different species of microalgae. For example, some have suggested the screening of individual algae for use in a polyculture system. Others have described the growing of a consortium of microalgae for biomass production and for production of bioenergy. Other references teach using a consortium of two or more species of algae for the production of biomass and/or for production of particular algal lipid, proteins, carbohydrates constituents. However, no one discloses controlling the culture conditions for affecting either flocculation and/or settling of the consortium of microalgae or either for affecting adhesion of the microalgae to surfaces of the bioreactor.

Cultivation of algae under conditions in which the cells become deficient in nitrogen, thereby causing the cells to produce long chain polymers having flocculating properties is known in the art. However, the culture of a consortium of multiples algal species, while controlling the properties of the algal cells to affect their flocculation and/or settling or to affect adhesion of the algal cells to surfaces of the reactor is not known in the art.

Thus, there exists a need for more robust, more easily parametrable, and controllable methods and systems for the culture of microalgae. In particular, there is a need for methods and systems for culturing and growing a consortium of microalgae in non-sterile cultures conditions, especially for the production of microalgae having properties and characteristics that can be adjusted and adapted as a function of proposed applications and desired results. More particular examples of desired controllable properties includes promoting flocculation and/or settling of the consortium of microalgae and/or minimizing adhesion of the microalgae to surfaces of the bioreactor or its components (e.g. optical elements). Controlling these properties may facilitate and/or promote harvesting of microalga and/or optimize productivity of the culture system. Methods and systems comprising controlling culture conditions for affecting proteins, carbohydrates and/or lipids content of the consortium of microalgae are also desirable.

SUMMARY

According to a first aspect, the present invention pertains to a method for the culture of microalgae, comprising:
  providing a consortium of at least two living species of microalgae;
  culturing under illumination said consortium in a controllable bioreactor and under non-sterile aqueous culture conditions; and
  controlling the culture conditions for affecting at least one of the following output: (i) flocculation and/or settling of said consortium of microalgae; and (ii) adhesion of the microalgae to surfaces of the bioreactor;
wherein the culture conditions are controlled to promote (i) and/or to minimize (ii), without adversely affecting growth of the consortium of microalgae.

As used herein, the term "controlling", when referring to the culture conditions, means selecting, adjusting, modifying the culture conditions and/or any modifiable culture parameter (e.g. agitation, illumination, gas, nutrients, temperature, pH, etc.).

As used herein, the term "affecting", when referring to a particular culture output, means influencing, perturbing, modifying, to obtain a desirable result.

As used herein, the term "without adversely affecting growth" means a minimal algal proliferation or growth measured by a photonic yield value lower than about 196 photon mole/captured $CO_2$ mole.

The value of 196 is not arbitrary and is based on the measured PY value reported in Table 1 for reactor R5 (141±55), that value corresponding to culture of algae in a "control" reactor exposed to direct sunlight, and not comprising any optical element. In certain embodiments, the control system may be "better" or "more efficient" in terms of minimal algal proliferation or growth than the reactor R5 and it can have a measured photonic yield value lower than about 196 photon mole/captured $CO_2$ mole, including but not limited to values of ≤150, or ≤125, or ≤100 or ≤75 photon mole/captured $CO_2$ mole. For instance, Table 2 herein refers to a measured PY value of 99 photon mole/captured $CO_2$ mole for a 3 $m^2$ reactor (2000 L) exposed to direct artificial light, without any optical element.

In one particular embodiment, the control of the conditions of culture comprises regulating one or more of the following parameters:
  a) mixing of the consortium;
  b) the amount and/or type of nutrients provided to said consortium; and the quantity and/or type of nutrients furnished to said consortium of microalgae;
  c) the level of luminosity provided to the consortium.

In certain particular embodiments, the mixing of the consortium of microalgae is less than 10 cm/s, preferably an aqueous culture speed of about 1 cm/sec to about 10 cm/sec, or between about 1 cm/sec to about 5 cm/sec or between about 1 cm/sec to about 3 cm/sec.

In certain particular embodiments, the mixing comprises a gaseous bubbling at a flow rate of about 0.001 to about 0.1 volume of gas per volume of reactor per minute (VVM) or at about 0.003 to about 0.01 VVM.

In certain particular embodiments, the quantity and/or the type of nutrients are controlled in order to maintain a load in nitrogen less than 15 gN/m$^3$.day, preferably between about 0.9 gN/m$^3$.day and about 15 gN/m$^3$.day, or between about 0.9 gN/m$^3$.day and about 10 gN/m$^3$.day, or between about 0.9 gN/m$^3$.day and about 6 gN/m$^3$.day, or between about 0.9 gN/m$^3$.day and about 2 gN/m$^3$.day, or between about 0.9 gN/m$^3$.day and about 1.5 gN/m$^3$.day.

In certain embodiments, the culture conditions are further controlled according to a predetermined use of the consortium. For instance the predetermined use of may be biofixation of $CO_2$, elimination or capture of undesirable gaseous substances (e.g. CO, $SO_2$, $NO_2$ and COS), production of a protein-rich algal biomass, production of a lipid-rich algal biomass, production of a carbohydrate-rich algal biomass, etc.

According to other embodiments, the method further comprises the step of bubbling into the bioreactor a gas comprising one or more of the following gaseous substances: CO, CO2, SO2, NO2, and COS. Advantageously, the gas may originate from an industrial effluent, and it is injected into the bioreactor for purification.

According to certain embodiments, the method also involves an additional stage of collection of sediment and/or flakes, and the control of said culture conditions aims at maximizing the decanting of the consortium of microalgae. In one preferred embodiment, the collection of sediment and/or of flakes involves a collection of sediment and/or flakes deposited in a lower portion or at the bottom of the bioreactor.

In other embodiments, the level of illumination is increased by a system for tracking and/or distribution of sunlight.

According to another related aspect, the invention relates to method for the culture of microalgae, comprising:
  providing a consortium of at least two living species of microalgae;
  culturing under illumination the consortium in a controllable bioreactor and under non-sterile aqueous culture conditions; and
    (i) mixing the culture at a speed of about 1 cm/sec to about 10 cm/sec; or
    (ii) bubbling a gas at a flow rate of about 0.001 to about 0.1 volume of gas per volume of reactor per minute (VVM);
  wherein the mixing or bubbling promotes flocculation and/or settling of the consortium of microalgae.

According to a further related aspect, the invention relates to method for the culture of microalgae, comprising:
  providing a consortium of at least two living species of microalgae;
  culturing under illumination the consortium in a controllable bioreactor and under non-sterile aqueous culture conditions; and
  maintaining a load in nitrogen in the culture between about 0.9 gN/m$^3$.day and about 15 gN/m$^3$.day;
wherein said load in nitrogen minimizes adhesion of the microalgae to surfaces of the bioreactor (or internal components), without adversely affecting growth of the consortium of microalgae.

According to another aspect, the present invention pertains to a controllable aqueous system for the culture of microalgae, comprising:

a consortium of at least two living species of microalgae in an aqueous culture solution;
  a bioreactor forming an enclosure comprising said aqueous culture solution; and
  controlling means for controlling culture conditions of said consortium;
wherein the system operates under non-sterile culture conditions; and
wherein the controlling means are parametrable for (i) optimizing flocculation and/or settling of said consortium of microalgae and (ii) minimizing adhesion of the microalgae to surfaces of the bioreactor, without adversely affecting growth of said consortium of microalgae.

In one embodiment, the system's controlling means comprises a mixer for mixing the culture at an aqueous culture speed of about 1 cm/sec to about 10 cm/sec. In another embodiment, the system's controlling means comprises a nutrient controller for maintaining a load in nitrogen in the culture between about 0.9 gN/m$^3$.day and about 15 gN/m$^3$.day.

In another embodiment, the system's controlling means further comprises a gas injector for bubbling into the bioreactor a gas comprising one or more of the following gaseous substance: CO, $CO_2$, $SO_2$, $NO_2$, and COS. Advantageously, the gas is bubbled at a flow rate of about 0.001 to about 0.1 volume of gas per volume of reactor per minute (VVM) or at about 0.003 to about 0.01 VVM.

In certain embodiments for the method and the system, the controlling comprises maintaining a minimal microalgae concentration between about 70 mg/l to about 1000 mg/l of culture.

In certain embodiments for the method and the system, the controlling comprises maintaining the culture conditions at a temperature between about 9° C. and about 29° C., preferably between about 19° C. and about 23° C.

In certain embodiments for the method and the system, the controlling comprises maintaining the culture conditions at a pH between about 6.5 and about 8.5.

In certain embodiments for the method and the system, the consortium comprises indigenous species of microalgae.

According to certain embodiments of the method and the system, the bioreactor is an outdoor open bioreactor.

According to certain embodiments of the method and the system, the controlling of the culture conditions comprises regulating illumination of the consortium. Regulating illumination may comprises optimizing amount of sunlight exposure and/or sunlight intensity by using a sunlight distribution device. Regulating illumination may also comprises using a mechanical sun-tracking device.

Additional aspects, advantages and features of the present invention will become more apparent upon reading of the following non-restrictive description of preferred embodiments which are exemplary and should not be interpreted as limiting the scope of the invention.

BRIEF DESCRIPTION OF THE DRAWINGS

Having thus generally described the nature of the invention, reference will now be made to the accompanying drawings, showing by way of illustration example embodiments thereof and in which:

FIGS. 15A-15J are photographs of culture samples taken at the end of the different batches after 7 days of growth in the 2,000-liter system as described in Example 3. These photographs were taken with an optical microscope at magnification of either 100× (E and H), 400× (A, B, C, F, and G) or 1000× (D, I, and J)

DETAILED DESCRIPTION

Figure 1:
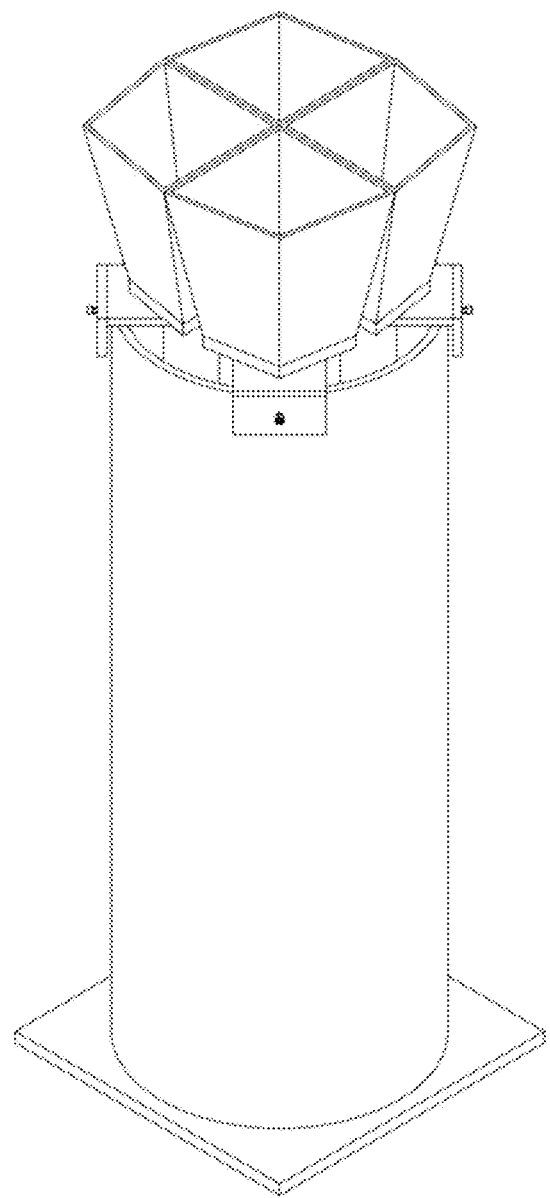
FIG. 1 is a diagram illustrating, from a side perspective view, a 20-liter reactor with four tulip-shaped optical elements, according to Example 1.

The present invention pertains to the field of the photosynthetic culture of microalgae and more particularly the growing of microalgae on an industrial scale. The invention particularly aims at utilizing the potential of microalgae for the sequestration of $CO_2$ (e.g., to improve the balance in the emission of greenhouse gases), for the cleanup of gaseous wastes, for the production of biofuels and for the production of biosourced products such as pharmaceuticals, cosmetics, nutraceuticals and foods (human and animal).

Consortium

Unlike the systems based on a monoculture of microalgae in sterile conditions, the present invention aims at growing a consortium of microalgae (i.e., a microalgae population composed of at least two different species) in non-sterile aquaculture conditions. Surprisingly, the inventors have discovered that the invention has many advantages and that it can address several problems of the prior art, such as:

making possible a culture in absence of antibiotics, bactericides, fungicides, and other substances;

making possible the use of indigenous strains of microalgae;

offering a more robust system of culture, in particular: less sensitivity to contaminants, less sensitivity to pH variations, less sensitivity to temperature variation; less sensitivity to a reduction in luminosity, ability to adapt very quickly to stresses in regard to nutrients, less sensitivity to toxic gas components;

facilitating the formation of flakes (flocculation) and decanting for easier harvesting;

minimizing adhesion of the microalgae to internal surfaces of the bioreactor and internal components (e.g. optical elements);

making possible a control and regulation of the protein, carbohydrate, and/or lipid content of the microalgae;

enables sustained growth in a medium containing few nutrients, fertilizer, etc., especially in a nitrogen-poor medium;

enables good growth and substantial yields, even with little stirring or agitation; and in the context of a use of indigenous strains for a large-scale outdoor deployment, better social acceptance as compared to genetically modified strains.

Several species of microalgae can be used in a consortium according to the invention and a person skilled in the art will be able to determine which species of microalgae should be used depending on various predetermined uses and factors (e.g., sequestration of gas or production of an algal biomass intended for consumption or instead a biofuel, etc.). For example, the microalgae making up the consortium could be chosen from the following non-exhaustive list: *Ankistrodesmus, Botryococcus, Chlorella, Chlorosarcina, Cryptheco-dinium, Cyclotella, Dunaliella, Euglena, Gracilaria, Hantzschia, Nannochloris, Neochloris, Nitzschia, Phaeodactylum, Protococcus, Sargassum, Scenedesmus, Schiochytrium, Stichococcus, Tetraselmis, Thalassiosira*, etc.

It is also possible to use genetically modified or isolated species. In certain preferred embodiments, the consortium is composed of indigenous species, for example, local indigenous species taken from a water course (river, stream), a body of water (lake, ocean) or a basin (reservoir, water treatment center), etc. The consortium can be formed randomly (any given indigenous sample) or be constructed precisely, taking into account various economic, climatic, and other specific aspects. For example, one can form a specific consortium by mixing together assemblages of known species, such as substantially pure samples of microalgae, by mixing several samples coming from a monoculture, etc.). One can also form a consortium adapted to the local conditions (temperature, luminosity, etc.) from local indigenous species. One can also influence the formation of the consortium to favor the growth of one species at the expense of another, by modifying the culture conditions (e.g., temperature, nutrients, luminosity, pH, toxic compounds, etc.).

One can choose to vary the composition of the consortium, and the total quantity of microalgae making it up as a function of different predetermined factors and uses, such as: for the sequestration, elimination and/or capture of gas; for the production of an algal biomass rich in protein, lipid, and/or carbohydrate; for the production of an algal biomass intended to be transformed into a biofuel, etc. In particular, it may be advantageous to maintain a minimal concentration of microalgae in the culture system in order to maintain the survival of desired populations and/or limit the growth of undesirable species (non-useful microalgae, bacteria, etc.). In certain embodiments, one maintains in the culture medium a concentration of microalgae from around 70-100 mg/l to more than 1000 mg/L of culture.

Flocculation and Settling

According to the present invention, it is possible to regulate one or more of the outputs associated with the culture of microalgae, such as the flocculation and/or settling of the consortium of microalgae.

According to the present invention, the term "flocculation" generally encompasses the formation of flakes and the aggregation of microalgae. According to certain embodiments of the invention, the flocculation favors a settling of flakes of microalgae at the bottom of the bioreactor. The control of the flocculation and/or the settling can be desirable, since it can assist and simplify collecting or harvesting the microalgae. In fact, the accumulation of the microalgae at the bottom of the bioreactor can enable the obtaining of a more concentrated material, thus limiting the efforts for dehydration of the harvested microalgae.

The flocculation can be encouraged and controlled in various ways. According to one embodiment, the flocculation is encouraged by minimizing the agitation inside the bioreactor. According to one embodiment of the invention, the agitation inside the bioreactor is reduced and it is accomplished by a controlled injection of a gas, preferably $CO_2$, in the bottom of the bioreactor. According to certain embodiments of the invention, the gas is bubbled at a flow rate varying from about 0.001 to about 0.1 volume of gas/volume of reactor/minute (VVM), or preferably at rates varying from about 0.003 to about 0.01 VVM. Additional suitable modes of agitation may comprises agitation by paddle or propeller, or pumping of the algae to the surface to reinject these algae at the bottom of the bioreactor.

Flocculation can also be encouraged and controlled by influencing the species of algae composing the consortium in order to favor the growth of a "flocculating" species at the expense of another species less inclined to flocculate. This can be done for example, by modifying the culture conditions, such as the temperature, nutrients, luminosity, pH, age of the culture, etc.

According to the present invention, it is possible to obtain a sufficient growth of microalgae even by minimizing the agitation inside the bioreactor. This finding is surprising, since the agitation generally produces better yields by providing the microalgae with a better access to light (i.e. at the surface of the reactor). Surprisingly, the inventors have shown that the culture of a consortium according to the present invention, with an agitation <9 cm/s and as low as 1-2.5 cm/s, has made it possible to achieve yields similar to an agitation of 10-25 cm/s (see Example 5). A reduced agitation (e.g., less than 10 cm/s or less than 5 cm/s) is advantageous, since it permits to reduce the costs of biomass production. In a preferred embodiment, the invention combines the use of a consortium of algae together with (1) a slight agitation and (2) a system of light diffusion. This combination is particularly advantageous for obtaining an algal biomass that is decanted, thereby allowing harvesting at the bottom of the reactor. Recovery at the bottom of the reactor can be done in various ways know in the art, including aspiration, scraping and the like.

Biochemical Content of the Algae and Nitrogen Load of the Culture

According to the present invention, it is also possible to regulate the protein, carbohydrate and/or lipid content of the consortium of microalgae.

According to one embodiment, one can regulate the algae biochemical content of the algal cells by influencing the particular composition of the consortium (i.e., the population of algae species) in order to encourage the growth of particular species at the expense of another. This can be done in various ways, for example, by modifying the culture conditions (e.g., temperature, nutrients, luminosity, pH, etc.).

According to one preferred embodiment, one can regulate the protein, carbohydrate and/or lipid content of the consortium of harvested microalgae by controlling the nutrient load of the culture, especially by limiting the quantity of nitrogen (i.e., causing a deficiency) that is available in the aqueous culture medium.

According to one particular embodiment, a low nitrogen load in the culture (i.e. <15 $gN/m^3$.day, <10 $gN/m^3$.day, <6 $gN/m^3$.day, <5 $gN/m^3$.day, <4 $gN/m^3$.day, <3 $gN/m^3$.day, <2 $gN/m^3$.day, <1 $gN/m^3$.day) means that the algae harvested have a lower protein content (e.g., 25%, 50%, 75%, 100%, 125%, 150%, 200%, 300%, or >300% less), as compared to a culture with a nitrogen load of 30 $gN/m^3$.day. In certain preferred embodiments, the nitrogen load in the culture medium is between 0.9 and 6 g $N/m^3$.day.

According to one particular embodiment, a low nitrogen load (i.e. <15 $gN/m^3$.day, <10 $gN/m^3$.day, <6 $gN/m^3$.day, <5 $gN/m^3$.day, <4 $gN/m^3$.day, <3 $gN/m^3$.day, <2 $gN/m^3$.day, <1 $gN/m^3$.day) means that the harvested algae have a higher carbohydrate content (e.g. 25%, 50%, 75%, 100%, 125%, 150%, 200%, 300%, or >300% higher), as compared to a culture with a nitrogen load of 30 $gN/m^3$.day. In certain preferred embodiments, the nitrogen load in the culture medium is between 0.9 and 6 g $N/m^3$.day.

According to one particular embodiment, a low nitrogen load (i.e. <15 $gN/m^3$.day, <10 $gN/m^3$.day, <6 $gN/m^3$.day, <5 $gN/m^3$.day, <4 $gN/m^3$.day, <3 $gN/m^3$.day, <2 $gN/m^3$.day, <1 $gN/m^3$.day) means that the harvested algae have a higher carbohydrate content (e.g. 25%, 50%, 75%, 100%, 125%, 150%, 200%, 300%, or >300% higher), as compared to a culture with a nitrogen load of 30 $gN/m^3$.day. In certain preferred embodiments, the nitrogen concentration in the culture medium is between 0.9 and 6 g $N/m^3$.day.

The nitrogen load in the culture can be controlled in various ways. In one particular embodiment, the nitrogen load is controlled by adjusting the quantity of nutrients (e.g. fertilizers, effluents rich in N—P—K, etc.) provided to the consortium of microalgae.

The nitrogen used in the culture can come from various sources, especially manure and fertilizers such as Nutrafin Plant Gro™ (formulation of 30-10-10; N—$P_2O_5$—$K_2O$). One can also use, as the main nitrogen source, biological wastes and residue such as sludge and/or municipal waste water, farming wastes, and slurries which contain N—P—K. Preferably, the adding of nutrients to the culture is done in liquid form.

In certain embodiments, the source of nitrogen is controlled to obtain a nitrogen concentration varying between 0.5 mg/L and 5 mg/L of culture. A person skilled in the art knows how to verify the nitrogen load of a culture of microalgae and that person knows how to adjust this load in acceptable manner.

Thus, according to the principles defined in the present invention, one can modify according to a desired objective the nitrogen supply in order to control the production of biomass and/or vary the proportions of the cellular components. For example, if the microalgae are produced for the bioenergy industry and the production of lipids (biodiesel) or carbohydrates (ethanol or butanol), a low nitrogen supply will be the preferred operating mode. If the microalgae biomass is produced for its protein (e.g. animal nutrition, fertilizers, etc.), a nitrogen-rich supply will be preferred.

According to the present invention, different culture strategy can be developed by modifying the culture conditions, especially the nitrogen load and supply, in order to control the particular cellular components of the algal biomass, such as the lipids, proteins and carbohydrates. For example, for the lipids, one may be interested in encouraging the production of omega-3 or saturated lipids by the algae. For carbohydrates, one be interested in encouraging the production of starch, hemicellulose, etc. For protein, one may be interested in encouraging the production of polypeptides having pharmaceutical properties or proteins rich in certain amino acids (e.g. methionine).

One related aspect of the invention is the use of a low nitrogen load in the culture medium in order to reduce the adhesion of the microalgae to the various surfaces which the algae are contacted. Thus, by reducing the adhesion of the microalgae, one can limit the fouling of various elements, mechanical parts and electronic parts, including for instance the interior surfaces of the bioreactor or culture basin (walls, bottom), probes and sensor inside the bioreactor, the piping system, the optical elements that may be used to promote penetration and/or diffusion of light, etc. Limiting the adhesion of the microalgae may be advantageous to maximize the growth of the algae and the productivity, for example, by maximizing the diffusion of light and/or the luminosity inside the bioreactor, especially when using optical elements as described in the present examples.

According to certain particular embodiments, a low nitrogen load (i.e. <15 gN/m3. day, <10 gN/m3.day, <6 gN/m3.day, <5 gN/m3.day, <4 gN/m3. day, <3 gN/m3.day, <2 gN/m3.day, <1 gN/m3.day) makes it possible to reduce by 25%, 50%, 75%, 100%, 125%, 150%, 200%, 300%, or >300% the adhesion of the microalgae, as compared to a culture with a nitrogen load of 16 gN/m3.day. In certain embodiments, one controls the adhesion with a nitrogen load in the culture medium between about 0.9 gN/m3.day and about 15 gN/m3.day, preferably between about 0.9 gN/m3.day and about 10 gN/m3.day; more preferably between about 0.9 gN/m3.day and about 6 gN/m3.day, more preferably between about 0.9 gN/m3.day and about 2 gN/m3.day, and more preferably between about 0.9 gN/m3.day and about 1.5 gN/m3.day.

Gas

The culture of the consortium of microalgae in aqueous and non-sterile medium according to the present invention may prove advantageous for the elimination and/or capture of various chemical components and gaseous substances, like those coming from industrial smokestacks. These gases may include, but are not limited to, gaseous substances such as carbon monoxide (CO), carbon dioxide ($CO_2$), sulfur dioxide ($SO_2$), nitrogen dioxide ($NO_2$), carbonyl sulfide (COS), etc.

Thus, according to certain embodiments of the present invention, a gas to be purified is injected into the culture system/bioreactor. The gas can be injected using various acceptable ways, such as by bubbling or at the surface (e.g. controlled atmosphere). If need be, the gas can be heated, cooled and/or mixed with other components (e.g. nutrients such as nitrogen). The gas can be injected directly or in an air matrix. Since the injection of gas may influence the pH (generally causing an acidification), it is generally preferable to verify the pH of the culture and adjust it in order to maintain optimal culture conditions (i.e., preferably to maintain a pH varying from 6.5 to 8.5). A person skilled in the art will know how to verify the pH of a culture of microalgae and how to select and use appropriate means to adjust the pH in an acceptable manner.

The type and composition of the consortium (e.g., the species of microalgae, the provenance of the microalgae) can be designed and/or selected specifically for such a use. Furthermore, a consortium comprising microalgae species useful in the treatment of gases may be encouraged by injecting gases having a predefined gaseous substances or by injecting gases coming from industrial smokestacks. Indeed, a prolonged culture under such conditions should make it possible to eliminate from the consortium sensitive species of microalgae and encourage instead growth of resistant species more appropriate for the job.

Temperature

The desirable temperature for the culturing of the microalgae is variable and generally lies between 10-27° C. For strains of temperate climates, the optimum is generally between 10-27° C. and preferably around 16-27° C. For thermophilic microalgae, the optimum is generally between 40-70° C. and preferably around 45-50° C. For psychrophilic microalgae, the optimum is generally between 0-25° C. and preferably around 10-20° C. According to certain preferred embodiments of the invention, the mean temperature is between 24° C. and 29° C.

According the present invention, the optimal temperature can be adjusted as a function of the consortium of microalgae being used, the provenance of the microalgae, the particular species of microalgae that one wishes to encourage, the intended applications, etc. For example, a consortium comprising thermophilic microalgae could be encouraged or specifically selected for a use intended for biofixation of industrial $CO_2$, since the gases rejected by the industries may reach elevated temperatures. By using thermophilic algae able to grow in warmer culture medium (e.g. between 40° C. and 45° C.), one could thus reduce the costs associated with the cooling of these industrial gases or the cooling of the culture medium.

Bioreactor and Culture System

As indicated hereinbefore, one aspect of the invention concerns a controllable aqueous system. One particular innovative aspect of the culture system is that it comprises controlling means for controlling the non-sterile culture conditions of the consortium, the controlling means being parametrable for (i) optimizing flocculation and/or settling of the consortium of microalgae and (ii) minimizing adhesion of the microalgae to surfaces of the bioreactor, without adversely affecting growth of said consortium of microalgae.

As pointed out, the culturing of the consortium of microalgae is carried out in an aqueous and non-sterile medium. According to one particular embodiment, the culturing of the microalgae is done in a controllable bioreactor, the bioreactor forming an enclosure which contains said aqueous medium, including the consortium of microalgae.

The bioreactor can be of variable size (several liters to several millions of liters) and be located indoors or outdoors.

The bioreactor can be part of a closed system, such as a photobioreactor (PBR), or be part of an open system such as a pond or basin illuminated by sunlight. In certain preferred embodiments, the bioreactor is adapted for a large-scale industrial culture in a basin of 10 m³ to 250 000 m³ or more.

The culture system and the bioreactor comprise, or are coupled in a certain manner, to controlling means for controlling culture conditions and/or for controlling certain parameters of the consortium and the algae composing it, especially: i) the flocculation and/or the rate of settling of the consortium of microalgae; ii) the adhesion of the microalgae to the surfaces of the bioreactor; and/or iii) the protein, carbohydrate, and/or lipid content of the consortium of microalgae.

For example, the culture system and the bioreactor may comprise one or more external elements able to influence the culture conditions. These external elements may include, without being limited to: a distributor of nutrients (e.g. nitrogen), a gas injector (e.g. $CO_2$), elements for controlling of the temperature (e.g. heating or cooling elements, thermostat, etc.), elements for stirring or mixing (hydraulic pump, propeller, liquid injector, etc.), elements for collecting or harvesting the microalgae (filtration system, aspiration system, pumping system, centrifugation system, etc.), lighting modules (electrical light source, regulator of intensity and/or duration of lighting, sunlight distribution device, sun-tracking device, etc.), probes and sensors (temperature, pH, optical density, nutrients, gas, etc.) and the like.

According to certain embodiments, the culture system and/or the bioreactor incorporates a system for the tracking and distribution of light (particularly sunlight), such as one described in U.S. patent application Ser. No. 13/778,521 filed on 27 Feb. 2013 entitled "Sun tracking light distributor system" and U.S. Ser. No. 13/780,857 filed on 28 Feb. 2013 entitled "Sun tracking light distributor system having a V-shaped light distribution channel", both of which are incorporated by reference herein in their entirety.

According to certain embodiments, the culture system and/or the bioreactor incorporates a V-shaped light distribution system having a pivot assembly for V-shaped light distributors and/or a cleaning system such as those specified in PCT patent application No. PCT/IB2014/061790 filed on 28 May 2014 entitled "V-shaped light distributor system", which is incorporated by reference herein in its entirety.

Figure 16:
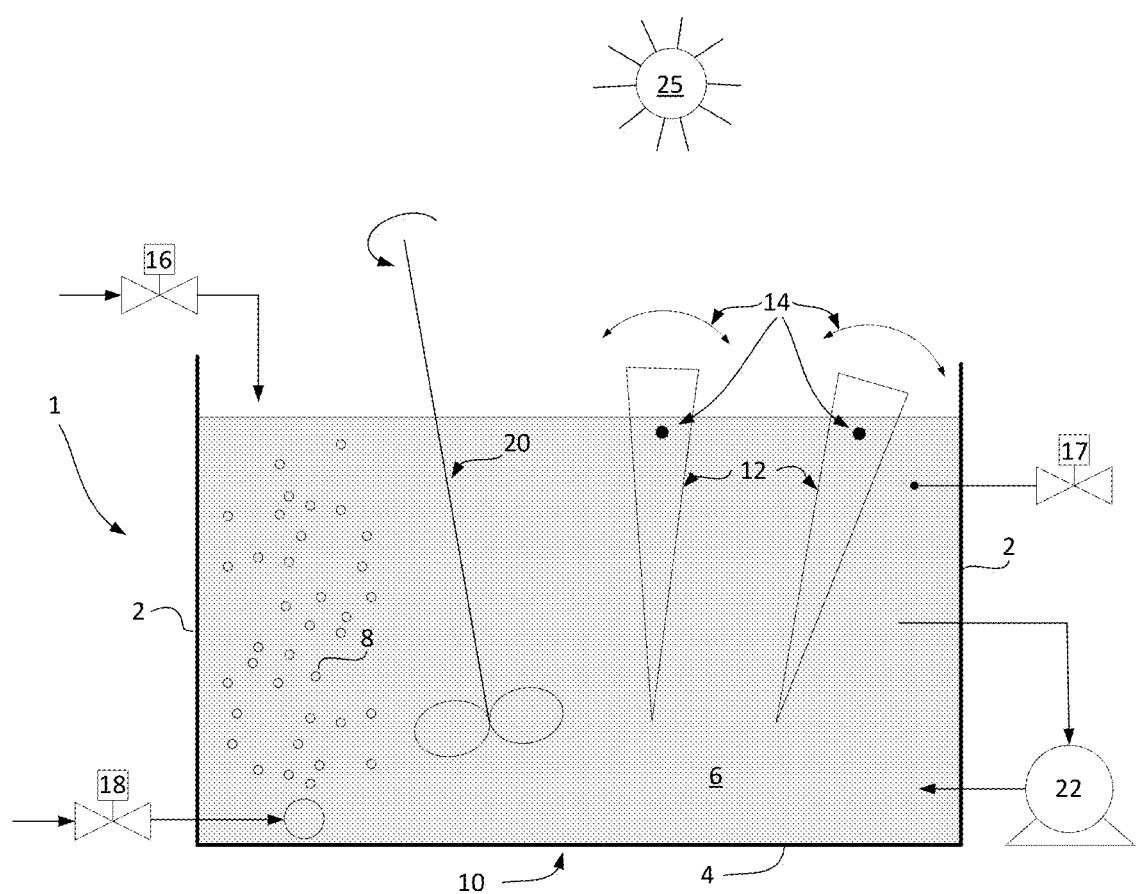
FIG. 16 is a drawing depicting a culture system, according to one particular embodiment of the invention.

One particular embodiment of a culture system according to the present invention is illustrated in FIG. 16. The culture system (1) comprises a bioreactor (10) comprising side walls (2) and a bottom wall (4) forming an enclosure. The bioreactor (10) comprises an aqueous culture solution (6) comprising a consortium of at least two living species of microalgae.

The culture system (1) comprises controlling means for controlling culture conditions of the consortium. The controlling means may consist of different control elements for affecting the culture conditions (nutrients, temperature, mixing, illumination, gas, pH, etc.)

In FIG. 16, the controlling means comprises mixers, illustrated as a propeller (20) and a hydraulic pump (22), for mixing the culture. The controlling means of FIG. 16 may comprise, in addition to a mixer or in replacement thereof, a gas injector (18) for bubbling gas (8), preferably $CO_2$, into the bioreactor. The controlling means of FIG. 16 further comprises a nutrient controller (16) for maintaining a load in nutrients (e.g. nitrogen) to a desirable level. The system preferably comprises one or more sensor (17) to continuously monitor various culture parameters such as the temperature, illumination, pH, etc.

In this particular embodiment, the bioreactor (10) is an outdoor open bioreactor and illumination of the algae is provided by the sun (25). According to this embodiment, the controlling means further comprises a sunlight distribution device (12) for increasing sunlight penetration into deeper portion of the reactor, and also a mechanical sun-tracking device (14) for optimizing alignment of the sunlight distribution device (12) with the sun, as it moves into the sky.

EXAMPLES

The following examples pertain to particular embodiments and are not meant to limit the invention, but simply to show its operation and its applications.

Premises:

"Photon yield" (PY) was used as a measure of the efficacy or productivity of the algal biomass. This theoretical value is around 10 moles of photon/mole of fixed $CO_2$. A low PY value indicates a good utilization of the light to fix $CO_2$, thus generating more algal biomass with less light.

Equation 1 presents a calculation method to estimate the photon yield of a culture system operating in continuous mode. The parameter "SS" (suspended solid) is measured following the purging of the system.

$$\text{Photon yield } (PY) = \frac{\text{Photon flux of culture system} \times \text{lighting duration}}{(\text{final } SS - \text{initial } SS) \times \text{reactor volume} \times \left(\frac{1,8}{1000/44}\right)}$$

Equation 1

For systems in batch operation, equationied due to the absence of purging, giving the following equation 2.

$$\text{Photon yield } (PY) = \frac{\text{Photon flux of culture system} \times \text{lighting duration}}{SS \times \text{purge volume} \times \left(\frac{1,8}{1000/44}\right)}$$

In equation 1 and equation 2, note the following:
The photon flux is in mole photon/hour;
The lighting duration in hours;
SS is expressed in mg/l;
The purge or reactor volume is expressed in liters;
1.8 represents 1.8 g CO2 per g of produced biomass;
1000 represents 1000 mg/g; and
44 represents the molecular weight of $CO_2$.

Example 1

Design and Fabrication of 20 L Reactors with Optical Tulip-Shaped Elements

Five reactors of 20 liters each were fabricated. Each reactor was made from a transparent plastic (acrylic) cylinder about 22 cm in diameter and with a total height of about 60 cm, or 10 cm of free space at the bottom for the agitation and injection of $CO_2$ as well as 5 cm free above the liquid level to prevent overflowing.

Figure 2:
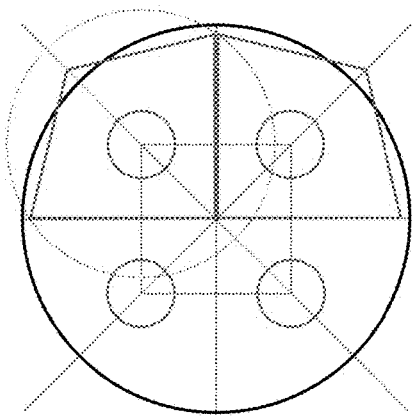
FIG. 2 is a diagram illustrating, from a top view, the localization of the four tulip-shaped optical elements arranged on top of the 20-liter reactor, according to Example 1.

Four optical tulip-shaped elements were inserted in each of the 20-liter reactor, as shown in FIG. 1 and FIG. 3A. The 4 tulips were distributed on a square of 8.5 cm on each side, as illustrated in FIG. 2 to cover the opening of the reactor. Each tulip was covered by a Fresnel lens cut to occupy around ¼ of the surface of the cylinder.

The performance was measured for three different values of light intensity incident on the tulips in a laboratory installation (FIGS. 3A and 3B).

Experiments were performed to determine whether the use of the tulip-shaped optical elements promotes the photon yield (PY). The effectiveness of a system with 4 tulips was compared to a conventional system without such tulip-shaped optical elements. The measurements of the PY are presented in Table 1.

TABLE 1

Test conditions and photon yields obtained for the optical elements of tulip type

| Reactor | Optical element and lighting intensity | Vol (l) | Gas (l/min) | Lighting | PY (moles of photons/ mole of $CO_2$) | Improvement factor |
|---|---|---|---|---|---|---|
| R1 continuous | 4 tulips at 50% solar intensity | 18.6 | 2 | 12/12 | 32 ± 8 | 3.7-4.4 |
| R5 continuous | Direct light 50% solar intensity | 7.4 | 0.7 | 12/12 | 141 ± 55 | |

The following conclusions can be drawn from the results of Table 1:

The use of tulip-shaped optical elements to distribute the light in the algal biomass augments the photon yield significantly, i.e by a factor between 3.7-4.4;

The gain in photon yield signifies that, at equivalent productivity, the system would occupy on average four times less surface than a conventional process without optical elements.

Example 2

Design and Fabrication of 20 L Reactors with Optical V-Shaped Elements

For basins of large dimension, longitudinal V-shaped optical elements would be preferred to tulip-shaped optical elements.

Figure 4:
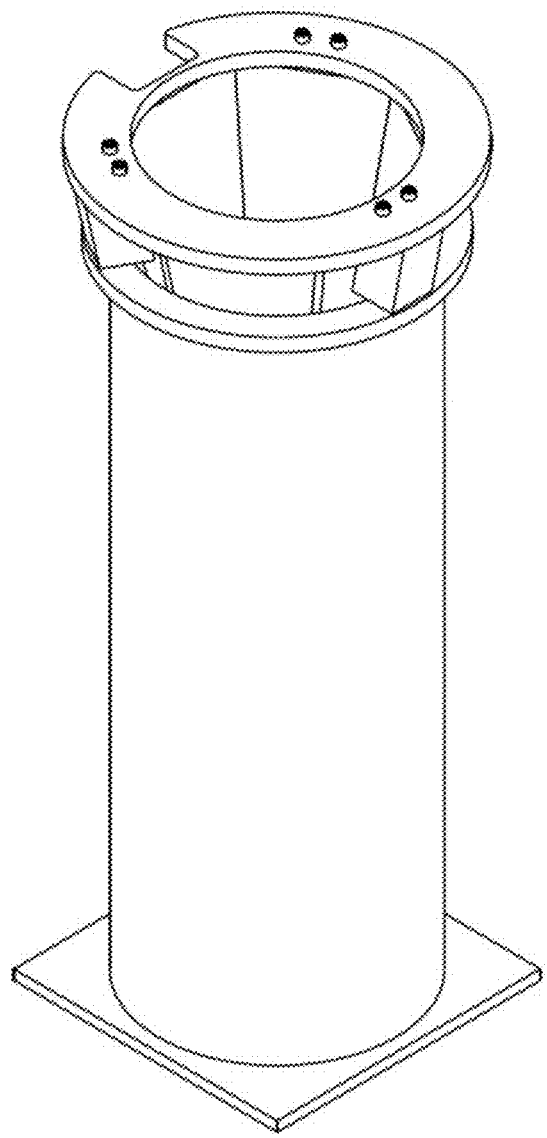
FIG. 4 is a diagram illustrating, from a side perspective view, configuration of a pyramidal V-shaped optical element mounted on top of a 20-liter reactor, according to Example 2.

For carrying out the following laboratory experiments, pyramidal V-shaped optical elements adapted to fit within the cylindrical shape of the 20-liter reactors where used. FIG. 4 shows the configuration of the pyramidal V-shaped optical elements. In this particular embodiment, the diameter of the internal opening is 19 cm and its height is 51 cm (corresponding to light dilution factor≅3.6×). Although these V-shaped optical elements are actually of a pyramidal shape, their optical operating principle is similar to that of longitudinal V-shaped element described in Example 3 below and, according to the present description, they will be referred to as "V-shaped optical elements".

Figure 5:
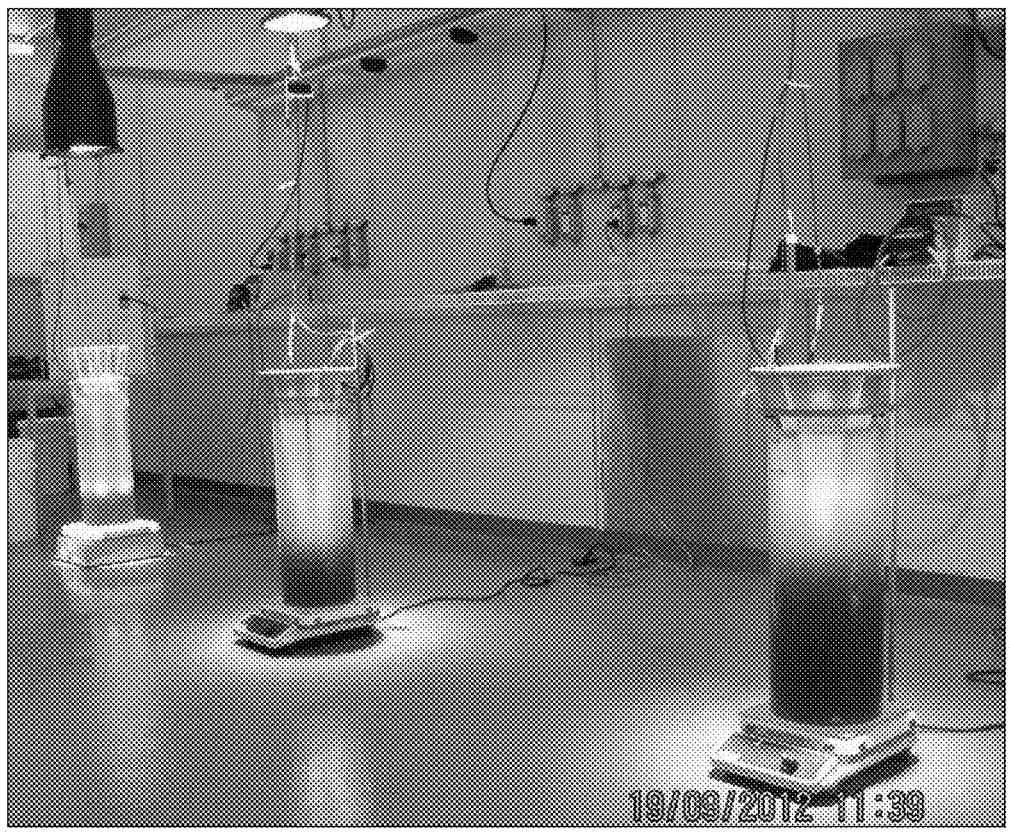
FIG. 5 is a picture of a laboratory installation showing 20-L reactors comprising tulip-shaped optical elements (left) and pyramidal V-shaped optical elements (middle and right)

FIG. 5 is a photograph showing the assembled reactors comprising the V-shaped optical elements (in the middle and on the right). In this picture, the first reactor on the left comprises tulip-shaped optical elements and is utilized as a reference during the laboratory experiments. The 20-liter cylinders were filled up to around 5 cm from the upper edge.

Example 3

Design and Fabrication of a 2000 L Reactor (3 $M^2$) with V-Shaped Optical Elements The design criteria for the prototype were based on results obtained in 20-liter reactors in combination with considerations of economics and applicability for a full-scale system.

Figure 6:
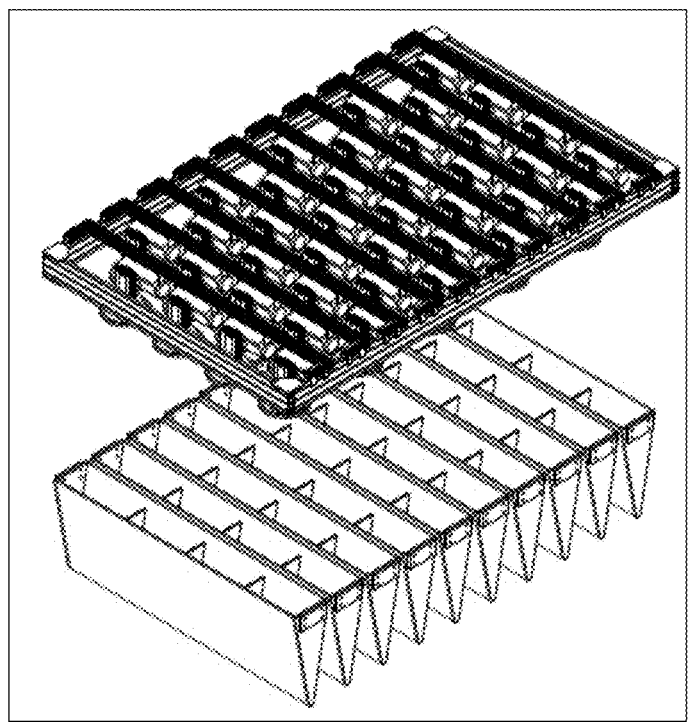
FIG. 6 is a diagram illustrating, from a side perspective view, a lighting module comprising a series of lights (top of the figure) and a series of ten longitudinal V-shaped optical elements (bottom of the figure), according to Example 2.
Figure 7:
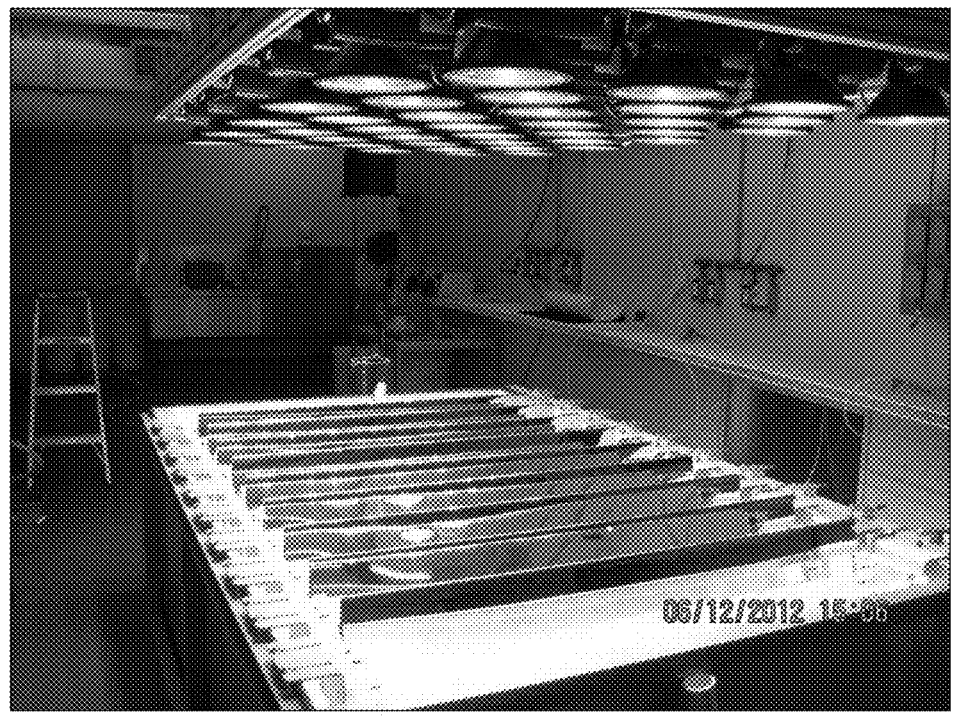
FIG. 7 is a picture of a 2000-liter reactor (3 $m^2$ basin) comprising a series of ten longitudinal V-shaped optical elements, and a lighting module above them, according to Example 3.

A laboratory prototype of 3 $m^2$ (2 000 liters basin) was fabricated and put to the test for a period of three months. V-shaped longitudinal optical elements were designed for the laboratory pilot of 3 $m^2$. The height of the V was set to ensure an optical dilution factor equivalent to that of the long V used during the tests of 20-liter reactors. FIG. 6 presents a diagram illustrating the lighting module and V-shaped optical elements. FIG. 7 shows an actual picture of the 3 $m^2$ basin with the V-shaped longitudinal optical elements and the lighting module above the basin.

In order to validate the effectiveness of the V-shaped longitudinal optical elements, experiments were performed with and without the V-shaped optical elements. The results of the measurement of the PY obtained in the 3 $m^2$ reactor are presented in the following Table 2.

TABLE 2

Photon yields obtained in the 3 $m^2$ reactor

| Optical element and type of lighting | Volume (l) | Gas (l/min) | Lighting | PY (moles of photons/ mole of $CO_2$) | Improvement factor |
|---|---|---|---|---|---|
| 10 long V-optical at 65% solar intensity | 1847 | 18 | 12/12 | 27 ± 2 | 3.7 |
| Direct light 65% solar intensity | 1847 | 18 | 12/12 | 99 | |

These results show that, for a scale of 2000 L (3 $m^2$), the use of the V-shaped optical elements makes it possible to achieve an improvement factor similar to that obtained during the experiments in reactors of 20 liters (Table 1).

Example 4

Startup of Systems Using Water Taken from the St-Lawrence River (Quebec Bridge)

Objective of the Experiments

The objective of these experiments was to validate that the use of microalgae originating from any given water could generate an adequate and well performing inoculum. For a large-scale application, the use of an inoculum coming from a local watercourse will be preferred. In this regard, a start-up based on an indigenous inoculum was carried out and the obtained consortium was used for specific series of experiments.

Description of the Experiments and Results

Figure 3:
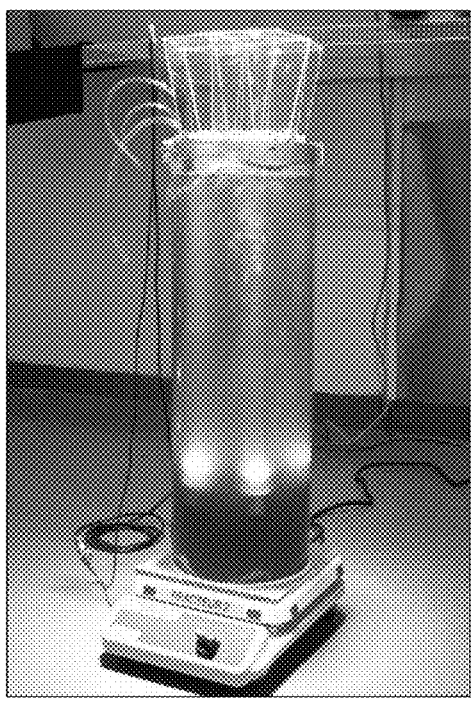
FIGS. 3A and 3B are pictures of a laboratory installation of 20-liter reactors with tulip-shaped optical elements, according to Example 1.
Figure 3:
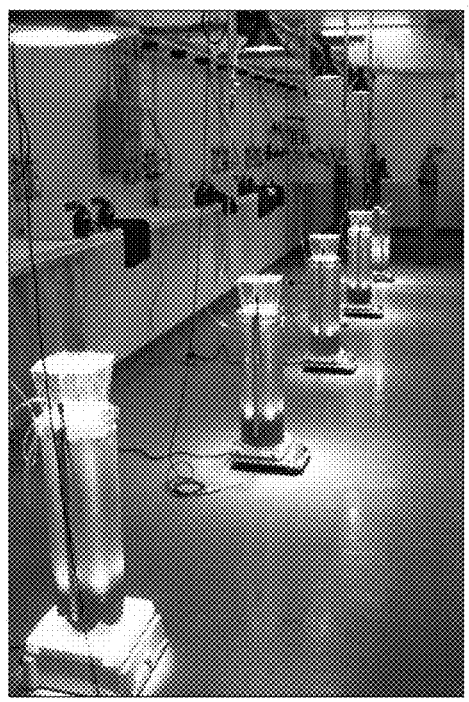

The start-up of the experiments was done with reactors of about 20 liters comprising tulip-shaped diffusion system of (FIGS. 1-3). The luminous intensity for these experiments was set at a value of 50% of the solar intensity for a period of 12 h/day. The nutrients Nitrogen (N) and Phosphorous (P) were furnished from horticultural 30-10-10 fertilizer and a solution of Nutrafin Plant Gro™ which furnished the essential trace elements. The pH was adjusted in a range of 6.5 to 7.5.

A volume of 100 L of water from the St-Lawrence River was collected on 1 May 2012 at the height of the Québec bridge at low tide. Upon reception, the water was filtered in a filter of size 297 μm in order to remove predatory organisms, crustaceans, sand particles, etc.

In all, six consecutive experiments were carried out in a 20 L reactor for testing different approaches and culture parameters. The most efficient sequence which generated a biomass with the best photon yields, was:

Rough filtering of the water;

Placing the river water in presence of light and with a dose of fertilizer corresponding to 710 mg/L of N and 31 mg/L of P. The use of fertilizer such as Nutrafin Plant Gro™ may be necessary on occasion to replace the micronutrients.

Leave this culture illuminated and do a transplanting of 10% of the volume every 9-10 days.

The number of transplants was four;

The reactor is inoculated with 10% of this volume of algae and a lower concentration of fertilizer on the order of 21 mg/L and 3 mg/L of N and P, respectively, is maintained with an addition of Nutrafin Plant Gro™ at 0.2 ml/L;

The reactor was illuminated with 50% of solar intensity and maintained in batch operating for more than 13 days;

An injection of $CO_2$ of 0.1% at 2 L/min was commenced starting on day 5;

Each day, a quantity of fertilizer on the order of 20 ml of 30-10-10 at 33 g/L and of Nutrafin™ at 0.2 ml/L was added to the 20 L reactor. This quantity of 20 ml could be lowered to 10 ml/day.

This biomass, once started in the 20 L reactor, was used in all of the subsequent experiments. After this, in more than 10 months of experiments, photon yields (PY) of 25 to 32 were frequently achieved in the optimized system.

According to the results obtained by these experiments, certain trends can be set forth:

Starting with a consortium of algae developed from a sample of water of the St-Lawrence River, it is possible to obtain well performing PYs of 25 to 32;

The startup process, although not optimal, calls for a growth without agitation, without aeration (static), in the presence of fertilizer, under lighting of 12 h/day with replenishments of 90% of the volume at 9 or 10 days;

This biomass can then be placed in a culture batch (20 L) for a period longer than one week and supplied with fertilizer at a load of 5 to 7 mgN/L.day under a lighting of 25 to 50% of solar intensity for 12 h/day. An injection of $CO_2$ (0.1% v/v) can be done after 5 days of growth at 2 L/min or less.

Upon startup of the bioreactors, the growth was initiated (batch) in the presence of a specific nutrient solution, intensity and duration of lighting. The quantity of biomass is monitored by means of the absorbance at 680 nm.

Figure 8:
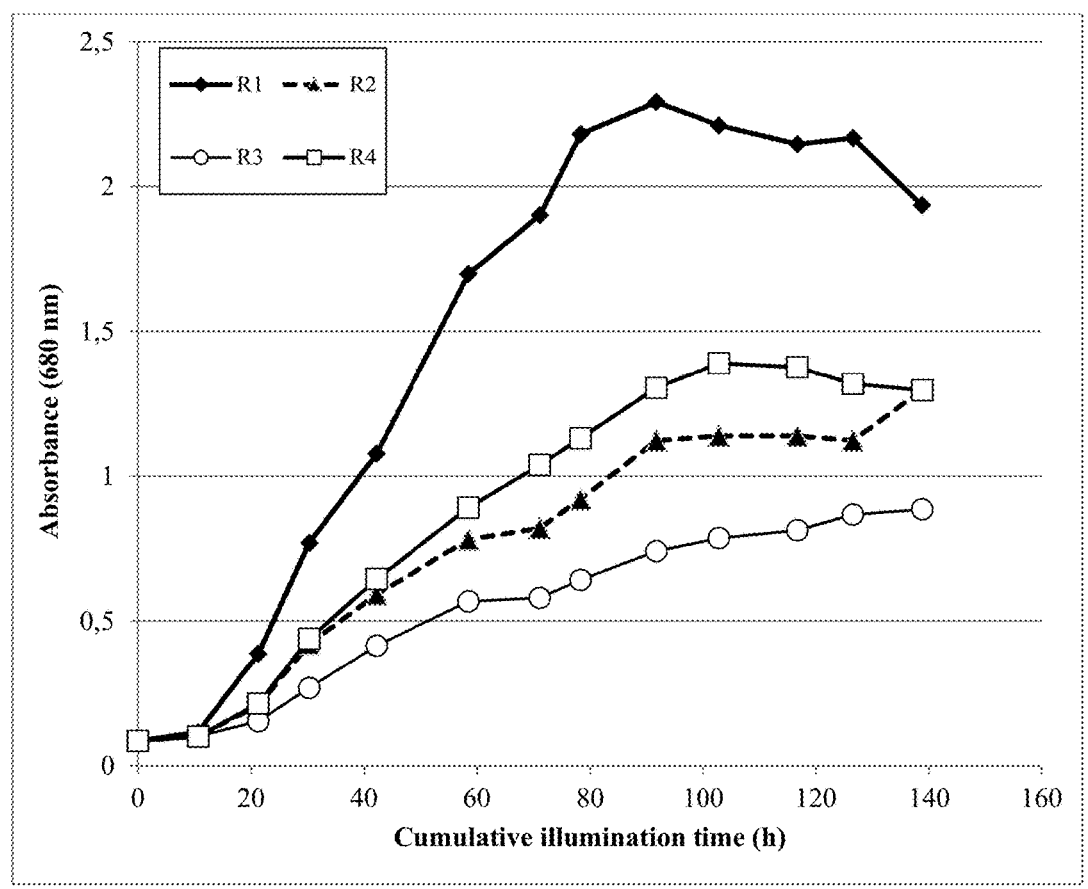
FIG. 8 is a line graph depicting growth of solutions of algae during startup under different lighting conditions (12 h/12 h), according to Example 4. R1=50% sunlight; R2 and R4—25% sunlight; R3=12% of sunlight)

The maximum rates of growth were calculated from the curves of FIG. 8. These values are compiled in Table 3 below. As anticipated, the highest growth rate is observed for the reactors having the greatest luminous intensity. These maximum values are measured between the 10th and 20th hour of illumination as compared to the systems at 12 and 25% of luminous intensity where the maximum growth was observed between the 20th and 30th hour of lighting. Likewise, the maximum cell densities of the cultures are directly proportional to the luminous intensity administered.

TABLE 3

Measurements of the maximum growth rates ($\mu_{max}$) estimated from consortiums cultivated in a batch

| Reactors | Type of lighting | $\mu_{max}$ $h^{-1}$ | $\mu_{max}$ $j^{-1}$ | Period of attaining $\mu_{max}$ hour of illumination |
|---|---|---|---|---|
| R1 | Diffuser 50% solar intensity | 0.11 | 1.21 | between 10-20 h |
| R2 | Diffuser 25% solar intensity | 0.08 | 0.71 | between 20-30 h |
| R3 | Diffuser 12% solar intensity | 0.06 | 0.56 | between 20-30 h |
| R4 | Diffuser 25% solar intensity | 0.08 | 0.76 | between 20-30 h |

Notes:
The growth rates in hours are calculated according to the illumination time. The growth rates in days are calculated according to the overall length of the experiment.

The growth rates calculated for the 4 reactors correspond to the values referenced in the scientific literature which can vary between 0.2 and 2.62 $day^{-1}$ depending on the species and different growth conditions (Cadoret and Bernard; 2008). These authors report a growth rate of 1.84 $day^{-1}$ for *Chlorella vulgaris*.

After the start-up, the systems were fed and purged according to an operation in turbidostat mode (controlled by the optical density or the cell density). The target values of the cell densities, estimated by absorbance at 680 nm, were set in the exponential area of the growth curve. Each day in the morning the absorbance value is noted down, a culture volume is removed and replaced with a volume of nutrient solution in order to re-establish the target value of absorbance.

Figure 9:
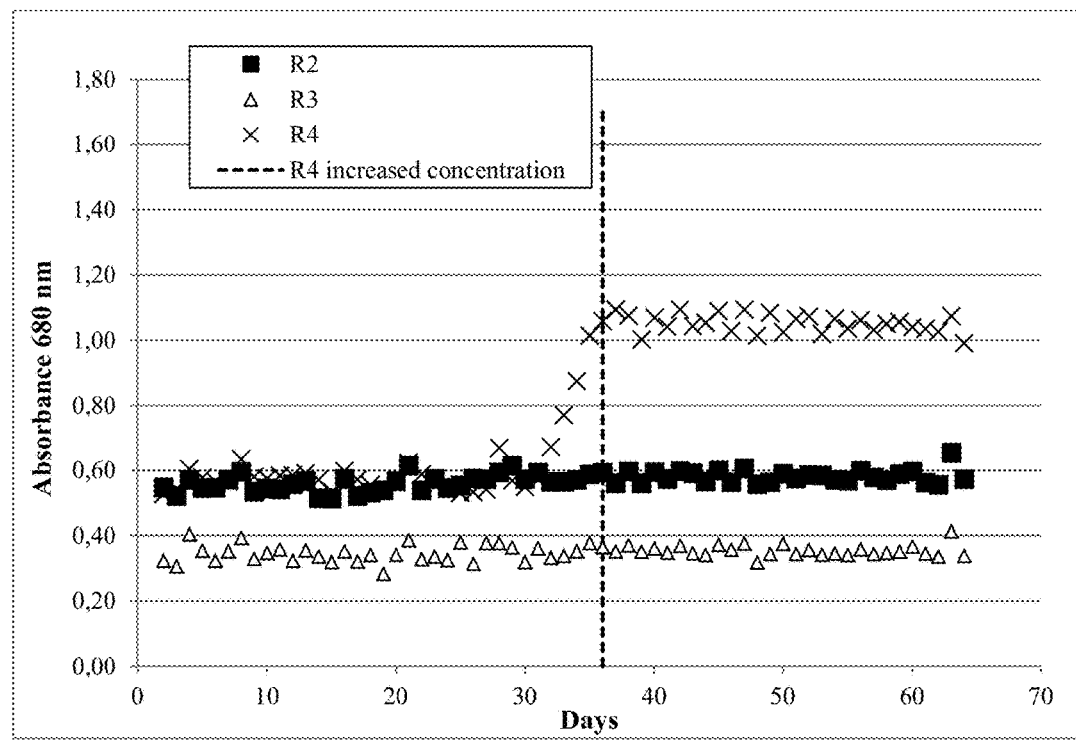
FIG. 9 is a line graph depicting tracking of the absorbance at 680 nm for 3 reactors during the experiments, according to Example 4. (R2=25% of sunlight; R3=12% of sunlight; R4=25% of sunlight). Key: x-axis=days.

FIG. 9 shows the tracking of the absorbance in 3 separate reactors on a daily basis. Overall, the behavior of reactors 2, 3 and 4 indicates a good stability in regard to variations of absorbance on a daily basis. The coefficient of variation (standard deviation/mean) varied between 2.7 and 6.3% for all the experiments.

An experiment in batch mode was also performed for several months by purging the system and keeping 10-25% of the culture of the consortium to restart the next batch. These experiments were carried out on the photobioreactor of 3 $m^2$ (2000 L) as described in Example 3 and illustrated in FIGS. 6 and 7. The agitation of this reactor was done by gas injection at 18 L/min for a liquid volume of 1847 L. The lighting was maintained at around 60% of the solar intensity for a period of 12 h/day. A system of pumped agitation with the help of a diaphragm pump and reinjection of the biomass at the bottom of the reactor was used for the experiments requiring a supplemental stirring.

Figure 10:
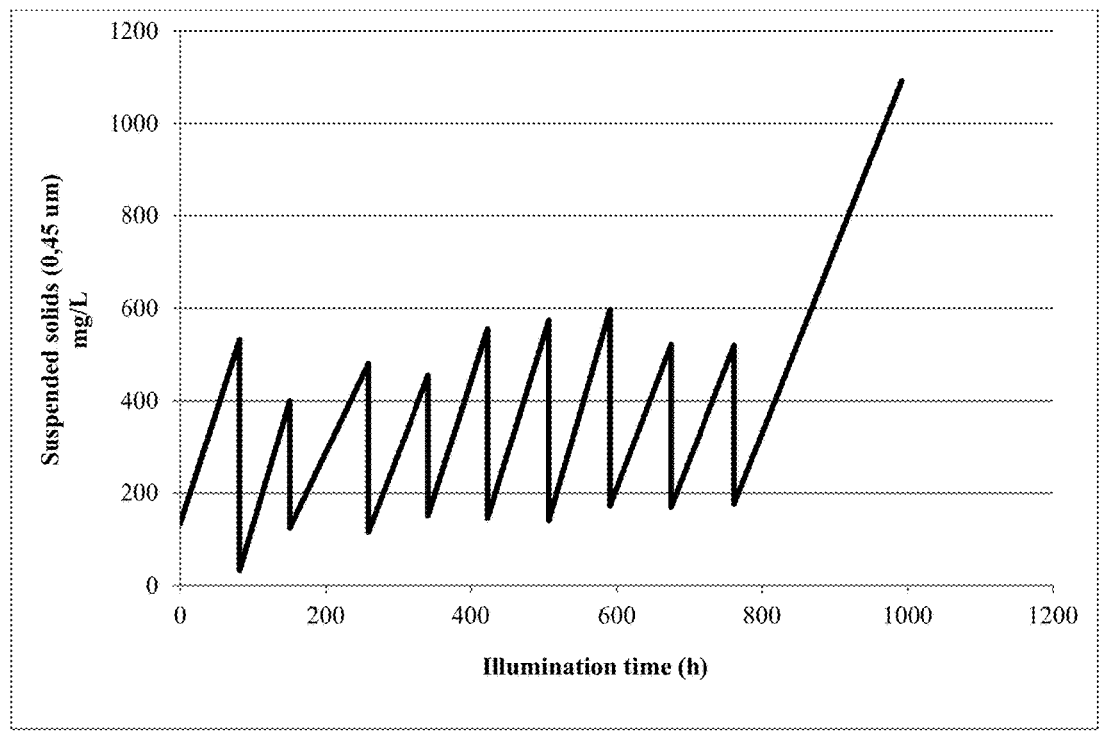
FIG. 10 is a line graph depicting batch growth experiments according to Example 4, during a tracking period of more than 2 months.

The results of the development of the biomass (SS or suspended solid) according to the batches are presented in FIG. 10. According to these results, it is possible, under non-sterile conditions and in an open system, to maintain an indigenous algal biomass in continuous or batch culture for several days.

Accordingly, unlike the prior art (e.g. U.S. patent application published as No. US 2010/0120095 and US 2010/0139265), the culture method and culture system of the present invention, with an indigenous consortium, does not require antibiotics or biocides to maintain the desirable characteristics and the performance of the culture.

The lipid contents of the consortium, for the batch and continuous cultures, are presented hereinafter in Tables 4 and 5, respectively. The results presented in these tables indicate that the consortium has a similar lipid contents, regardless of the mode of production (batch vs continuous). Likewise, the lipid contents are maintained in experiments performed at intervals of several months. For comparison, the lipid contents of the principal strains of microalgae of fresh water reported in the Oilgae Report Academic Edition (April 2011) are between 14-40%.

TABLE 4

Lipid content of the consortium for different batch cultures
(Photobioreactor of 2000 L with V-shaped optical element)

| # Batch | Lipid contents % d.w |
|---|---|
| 4 | 21 |
| 5 | 22 |
| 6 | 24 |
| 7 | 22 |
| 8 | 21 |

TABLE 5

Lipid content of the consortium for the continuous culture
(Photobioreactor of 20 L with tulip-shaped optical element)

| | Lipid contents % d.w. | |
|---|---|---|
| Reactors | T = 0 day | T = 47-50 day |
| R1 | 20 | 24 |
| R2 | 23 | 20 |
| R3 | 23 | 24 |
| R4 | 24 | 26 |

Example 5

Effect of Agitation on the Photon Yields and on the Settling of the Biomass

Objective of the Experiments

The objective of these experiments was to understand and measure the effect of agitation (mechanical and/or gaseous) on the biomass production and on the utilization of the photons. A process whose algal growth is well performing under conditions of slight agitation constitutes a very economical approach to production. A decrease in the agitation or the aeration could have direct impact on the growth of the algae or on their segregation in the reactor (settling or adhesion).

In order to verify this hypothesis, experiments were performed under different conditions of agitation. These experiments were arranged on the basis of industrial applications such as aerated ponds for which large surfaces are aerated and agitated.

Methods

Experiments to test the effect of agitation of the biomass on the PY were carried out on reactors of about 20 L provided with a tulip-shaped light diffusion system (FIGS. 1 to 3).

During the experiments, the light was set at around 50-60% of the solar intensity for all the reactors. The nutrients (N and P) were in excess in all the cases. The pH was adjusted in a range of 6.5 to 7.5. $CO_2$ was supplied to the system in concentration adapted to the gas flow for each reactor. All the experiments were carried out in a batch for a period of more than 100 h of illumination.

In addition, settling experiments were also carried out in a reactor of 200 L (3 $m^2$). Two additional experiments were performed in the 3 $m^2$ the reactor. The first one consisted in keeping only gas injection as the stirring method and measuring the vertical profile of SS. The other series of experiments consisted in adding a system of recirculation of biomass via a diaphragm pump at a rate of one volume of 1000 L recirculated at times. The diaphragm pumps are known for limiting cell breakage (Jaouen et al 1999). The biomass was pumped to the surface and reinjected at the bottom of the basin via a perforated piping to facilitate its dispersion. Several batch experiments were performed, each one lasting for around 7 days.

Results

The results of the effect of agitation on the placement of the algae in suspension are shown in Table 6 hereinafter.

TABLE 6

Effect of the agitation of the 20 L reactors on the suspension (mixing) of the biomass, as evaluated in terms of the absorbance measurement.

| | | Speed (cm/sec.) | | Absorbance (at 680 nm) | | |
|---|---|---|---|---|---|---|
| | | | | Before suspension | After suspension | Increase in |
| Reactor | Mixing/gas conditions | Bottom | Surface | T = 120 h | T = 126 h | absorbance (%) |
| R2 | Gas at 2,000 mL/min. and agitation at 4 with the aid of a magnetic stirring device. 0.1% $CO_2$. | 3 | 9 | 2.79 | 2.99 | 7 |
| R3 | Gas only, at 200 mL/min. 1% $CO_2$. | 2.5 | 4 | 2.72 | 3.31 | 22 |
| R4 | Gas only, at 60 mL/min. 3% $CO_2$. | 1 | 2.5 | 2.64 | 3.43 | 30 |

TABLE 6-continued

Effect of the agitation of the 20 L reactors on the suspension (mixing) of the biomass, as evaluated in terms of the absorbance measurement.

| Reactor | Mixing/gas conditions | Speed (cm/sec.) Bottom | Speed (cm/sec.) Surface | Absorbance (at 680 nm) Before suspension T = 120 h | Absorbance (at 680 nm) After suspension T = 126 h | Increase in absorbance (%) |
|---|---|---|---|---|---|---|
| R5 | Gas at 60 mL/min. and agitation at 4 with the aid of a magnetic stirring device. 3% $CO_2$. | 1.5 | 3 | 2.31 | 3.10 | 35 |

The findings reported in Table 6 definitively confirm that for a reactor operating at a low rate of agitation, the algal biomass can develop but it does not remain in suspension. Indeed, a manual suspension of the biomass provides for absorbance values that are higher than the value that was measured in the reactor using the agitation parameters defined in Table 6. The results of the absorbance measurements indicate that the biomass is growing well in reactors that are agitated at a low rate, but they also indicate that the biomass remains attached to the walls of the reactor or the biomass is decanted due to low shear forces. The presence of clumps ("flocs") was also observed for reactors R4 and R5. This fixation effect of the biomass was less pronounced for R2, which was heavily agitated and whose agitation speed was on the order of 9 cm/sec at the surface of the reactor (Table 6).

Table 7 provides a statistical comparison of the PY values for R2, R3, R4 and R5. Because of the nature of the experiments, few PY values were measured. When the 3 series in the experiment were performed, only the initial and final SS values were obtained.

TABLE 7

Comparative analyses of the effects of agitation and aeration on the calculated Photon Yield (PY) values ($\alpha = 0.05$) for 20 L reactors.

| Variables | Comparison | Obs. No. | PY Mean ± standard deviation | T-test $\alpha = 0.05$ | Conclusion |
|---|---|---|---|---|---|
| Gas flow | R3: 200 mL/min. | 3 | 41 ± 3 | 1.15 < 2.78 | The means are similar |
|  | R4: 60 mL/min | 3 | 44 ± 4 |  |  |
| Magnetic stirring | R4: not stirred | 3 | 44 ± 4 | 0.38 < 3.18 | The means are similar |
|  | R5: Stirred | 2 | 46 ± 9 |  |  |
| Flow and stirring | R2: 2000 mL/min. + stirred | 3 | 46 ± 9 | 0.34 < 2.78 | The means are similar |
|  | R4: 60 mL/min. + not stirred | 3 | 44 ± 4 |  |  |

The results of presented in Table 7 suggest that, for the ranges that were tested during these experiments, agitation or aeration has no effect on the use of photons by the algae. Accordingly, the use of an indigenous algae consortium under relatively low agitation conditions (1 to 3 cm/s) makes it possible to obtain a level of productivity that is similar to the one obtained with a more heavily agitated system (e.g. R2 with a speed of 3 to 9 cm/sec). For example, stirring speeds of 10 to 25 cm/s have often been proposed for open-pond systems on an industrial scale (Oilgae Report, Academic Edition, April 2011).

It is well known that collection or harvesting of the algal biomass constitutes a limiting stage in the implementation of procedures on an industrial scale. Accordingly, settling and/or bioflocculation may be an advantageous culture characteristics that could be exploited in order to facilitate harvesting of the algae (e.g. algae deposited at the bottom of the bioreactor).

Figure 11:
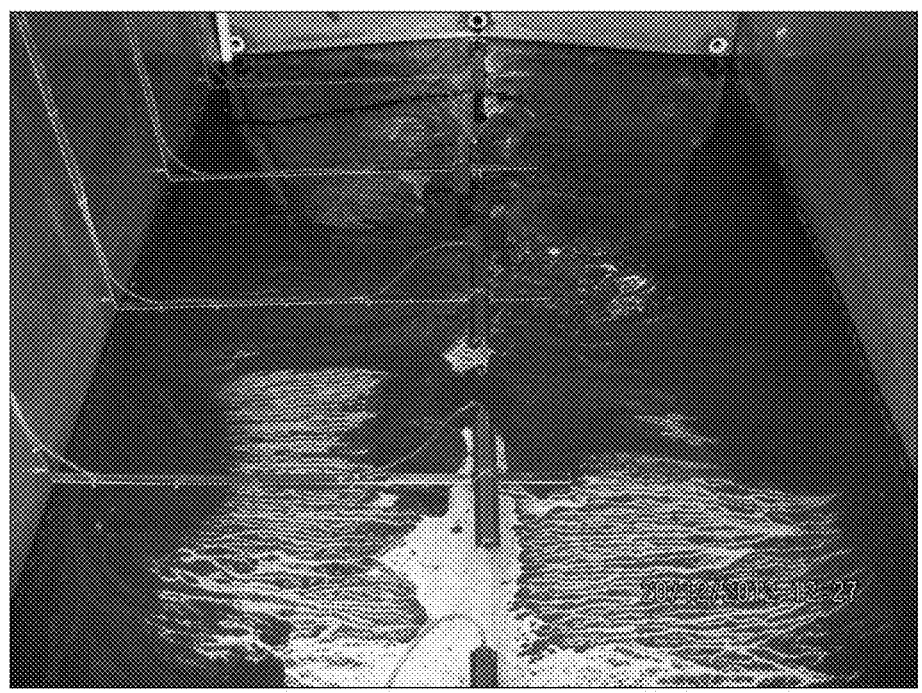
FIG. 11 is a picture of interior of an emptied 2,000 L reactor (3 $m^2$) showing appearance of the algal biomass, decanted without mixing (at the end of Batch 2), according to Example 5.

In the next series of experiments, vertical concentration profiles of the biomass were observed so that settling/adsorption in the reactor could be evaluated. In the absence of mechanical stirring, the algae decanted and deposited at the bottom of the reactor as shown in FIG. 11. The dryness of the decanted biomass sludge at the bottom of the reactor was on the order of 21% (210,000 mg/L) dry matter, which is much greater than the operating concentration of the reactor (approximately 1000 mg/L).

The vertical profile of the biomass was observed in the 3 $m^2$ reactor, which was agitated solely by means of gas injection. Samples were taken at five depths and in two different areas in the reactor (V2-V3 and V8-V9), and the SS values were measured. The results are shown in FIG. 12.

Figure 12:
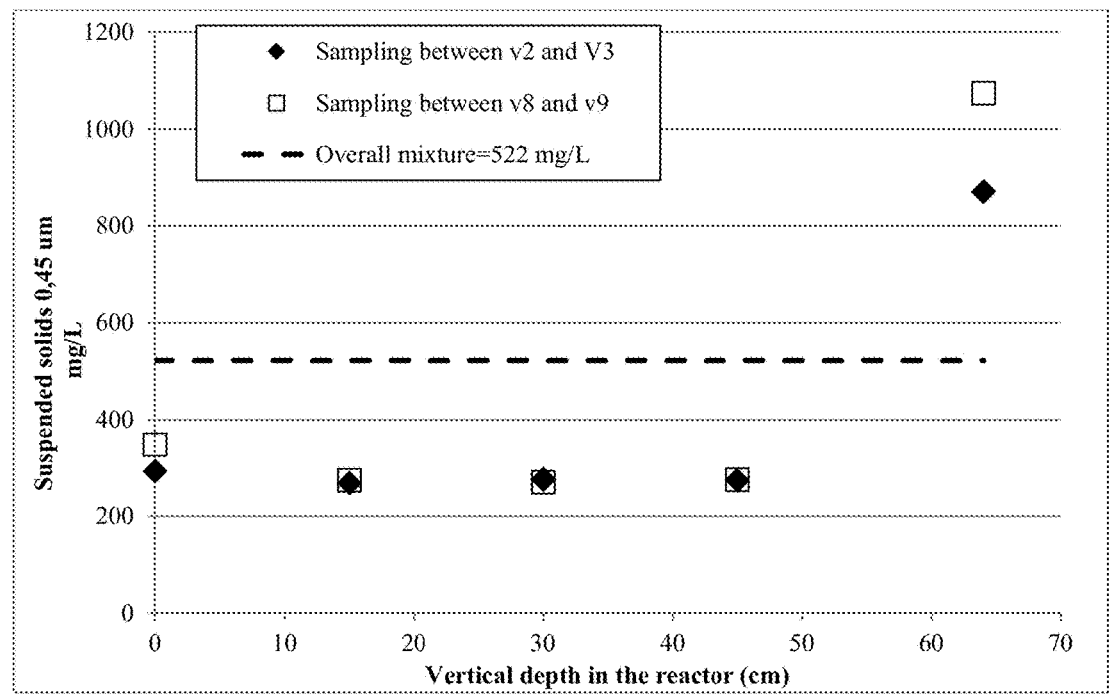
FIG. 12 is a dot graph depicting vertical profile of the SS values in the 2,000 L (3 $m^2$) reactor, agitated solely by means of the injection of gases at 0.009 VVM (end of Batch 9), according to Example 5.

FIG. 12 shows that the biomass concentration remains essentially constant at ±270 mg/L for a depth of 0 to 45 cm. Conversely, the biomass is more concentrated at the bottom, reaching values in excess of 800 mg/L. These results suggest that settling could be a feasible approach for a simplified harvesting microalgae at high concentrations.

As a supplement, concentration values for the biomass in suspension, with or without agitation, for the 3 $m^2$ reactor are shown in Table 8 below.

TABLE 8

SS values of the algal biomass collected at the surface of the 3 $m^2$ reactor, for different growth batches with or without agitation by means of recirculation.

| Batch | Mixing/gas conditions | Measured SS (mg/L) Before suspension | Measured SS (mg/L) After suspension | Increase in concentration (%) |
|---|---|---|---|---|
| 3 | Gas injection (0.009 VVM) and recirculation (1,000 L/h) | 397 | 420 | 5 |

TABLE 8-continued

SS values of the algal biomass collected at the surface of the 3 m² reactor, for different growth batches with or without agitation by means of recirculation.

| Batch | Mixing/gas conditions | Measured SS (mg/L) Before suspension | Measured SS (mg/L) After suspension | Increase in concentration (%) |
|---|---|---|---|---|
| 4 | Gas injection (0.009 VVM) and recirculation (1,000 L/h) | 458 | 481 | 5 |
| 5 | Gas injection (0.009 VVM) and recirculation (1,000 L/h) | 394 | 455 | 13 |
| 9 | Gas injection (0.009 VVM) only | 348 | 522 | 33 |

The results presented in Table 8 indicate that agitation makes it possible to keep almost all of the biomass of the system in suspension. Accordingly, measurements of the biomass in suspension represent between 87% and 95% of the system's biomass. When injection of gases was used as the only mixing method, 33% of the biomass was found on the bottom or adhered to the optical elements. Accordingly, an operating procedure using only gas injection could be employed in order to obtain both, a good productivity and a settling of the biomass.

Accordingly, the combination comprising the use of a consortium of algae, paired with a low level of agitation and a light-diffusion system capable to increase productivity by a factor of 3.5 or 4, makes it possible to obtain an algal biomass that can be decanted, thus further enabling its recovery from the bottom of the reactor.

In summary:

A very modest mixing does not affect the conversion of light into biomass for a batch culture over a period of approximately ten days;

A very modest mixing encourages settling;

Concentration of biomass may be from 2 to 4 times higher in settling regions than at the surface when the system is only modestly agitated;

Continuous very modest mixing of the biomass, combined with an aspiration system located at the bottom of the reactor or basin, appears to be a promising approach for the harvesting and dehydration of the biomass; and Modest mixing also appears to encourage agglutination/flocculation (i.e., the formation of flocs) of the algae, which may constitute an advantage in terms of energy and harvesting.

Example 6

Effect of the Dose of Nutrient on the Photon Yields and on the Chemical Composition of the Microalgae Objectives of the Experiments The objective of these experiments was to evaluate the effect of the dose of nutrients (N and P) on the yields of the culture system and on the composition of the biomass.

Methods

Experiments were performed in order to test different doses of nutrients for multiple batches of culture in a photobioreactor having a capacity of 3 m² (2,000 L), as shown in FIG. 6 and FIG. 7. This reactor was stirred by means of gas injection (1% $CO_2$) at a flow rate of 18 L/min for a liquid volume of 1,847 L. The lighting was kept at approximately 60% of solar intensity for a period of 12 hours/day. The agitation system, which was based on recirculation, was implemented by means of pumping from the surface, with the aid of a diaphragm pump, with reinjection of the biomass at the bottom (1,000 L/hour). The pH was adjusted to a value within the range from 6.5 to 7.5. The duration of the experiments ranged from 84 hours to 120 hours.

The fertilizer that was used was a horticultural fertilizer with a 30-10-10 ($N-P_2O_5-K_2O$) formula. A concentrated stock solution (fertilizer concentration of 33 g/L) was prepared with dechlorinated tap water. The stock solution contained a final concentration of 9.9 g/L of N, 1.4 g/L of P, and 2.7 g/L of K.

The final N/P ratio of the culture solution was 5.5. That value is within the range of ratios of 2.5 and 10 for which it has been suggested that consumption of the N and of the P should be complete (Li et al., 2012). The various nutrients loads that were tested during the experiments ranged from 0.9 to 16 g N/m³ per day, corresponding to a concentration of 6 to 112 mg/L over a period of 7 days.

Results of the Experiments a) Algae Growth

The results of the effect of the fertilizer loads are shown in Table 9 below. According to these findings, a load of 0.9 to 6 g N/m³ per day appears to be sufficient to generate good microalgae growth and to ensure almost complete consumption of the N and of the P.

TABLE 9

Effect of the nitrogenous loads on algal growth in batch operating mode (2,000 L reactor with a capacity of 3 m²).

| Experiment No. | N load (in g of N/m³ per day) | Final PY |
|---|---|---|
| 2 | 16.1 | 30 |
| 7 | 6.1 | 27 |
| 6-11 | 5.4 | 28-32 |
| 8-9 | 1.5 | 25-32 |
| 10 | 0.9 | 32 |

With a low nitrogen load (<1.5 g N/m³ per day), a significant difference in the color of the algae was observed. Their color was paler (yellowish-green) than that of algae that had been cultivated with higher nitrogen concentrations (dark green). This difference in color illustrates the rapid adaptation of the consortium, through a change in its pigmentation, in response to nitrogen stress. One worthwhile positive finding is that productivity (PY) was not affected in any way by the nitrogen load (Table 9).

The prior art suggests a low growth for a pure culture of *Chlorella vulgaris* with N concentrations of 10 mg/L (Tam and Wong, 1996). In the present experiments, the loads that were tested ranged from 0.9 to 16 g N/m³ per day, corresponding to a concentration of 6 to 112 mg of N per liter over a period of 7 days. Thus, it was surprising to find that, according to the principles of the present invention, and contrary to the published report, the use of a consortium of algae allows a very good adaptation to low doses of nutrients, while maintaining constant productivity levels (i.e., a constant PY).

Furthermore, apart from the change in color due to the lack of nitrogen, it was noted that at low doses of nitrogen there was little adsorption of the microalgae on the optical elements. After seven days of growth at a low N load (1.5 g N/m³ per day), very little biomass was adhered to the surface of the optical elements (not shown). Since the optical elements were essentially free from algae they could easily be cleaned, i.e. simply by a stream of water, with no mechanical intervention.

To the contrary, with a load on the order of 6.9 g N/m³ per day, much more biomass was adhered to the surface of the optical elements (not shown). Since the optical elements were essentially covered with algae, the cleaning of the optical elements was more difficult, requiring a stream of water in conjunction with mechanical cleaning and with the aid of a rubber scraper.

Thus, according to the present invention, it may be advantageous to use reduced loads of fertilizer in order to limit the fouling of internal surface of the reactor and/or its optical elements.

In summary, according to the principles of the present invention:

The actual nitrogen requirement, without affecting the photon yield, is between 0.9 and 6 g N/m³ per day. This means that municipal wastewater could be used to meet the nitrogen requirements.

The algal biomass consortium has the ability to adapt very rapidly to nutrient-related stresses. The growth performance of the algae is scarcely affected, although a change in pigmentation has been observed.

The use of a low nitrogen load has the further advantage of reducing the adhesion of the algae to the internal surface of the reactor and/or its optical elements, thereby limiting the fouling of those elements.

B) Composition of the Algae

The analysis of the effects of the nitrogen load on the absorption capabilities of the biomass was supplemented by analyses of the composition of the algae for different nitrogen loads.

The characterization was performed on three samples of biomass that were produced during experiments with the 2 m³ capacity reactor. Sample No. 1 is a composite that was obtained by mixing the biomass from two series of experiments lasting 9 and 7 days, respectively, and for which the respective nitrogen loads were 4.6 and 5.4 g N/m³ per day. Sample No. 2 came from an experiment that lasted 7 days, in which the nitrogen load was also 5.4 g N/m³ per day. A third sample was analyzed after an experiment that lasted 7 days, for which the nitrogen load was reduced to 1.5 g N/m³ per day.

Table 10 shows the results of the analyses of the major constituents of the algal biomass. The nitrogen load seems to affect the carbohydrate and protein content of the cellular constituents. In fact, for a low nitrogen load, the algae that were collected from sample No. 3 had a protein content that was lower (by more than half) than the protein content that was measured for the algae samples that were fed with a higher load (No. 1 and No. 2). Conversely, the same algae (from sample No. 3) had a carbohydrate content that was twice as high as the carbohydrate content of the algae that were cultivated at higher nitrogen concentrations (No. 1 and No. 2).

Table 11 shows the distribution of the lipid, carbohydrate and protein fractions according to the nitrogen load. What this means is that a nitrogen nutrition strategy would make it possible to control the production of biomass in order to vary the proportions of the cellular constituents of the algae, according to the product intended to be sold on the market. As shown in Table 11, a low-nitrogen strategy would favor the carbohydrate and fat fractions, to the detriment of proteins. Accordingly, if the algae are cultured for the production of bioenergy (i.e. the production of fats (biodiesel) or carbohydrates (ethanol or butanol)), then a low-nitrogen nutrients would be the preferred operating mode of the culture system. Conversely, if proteins are the desired products (e.g. for animal feed and/or for use as fertilizers), then preference would be given to nitrogen-rich nutrients culture system.

TABLE 10

Distribution of constituents in the algal consortium, according to their nitrogen loads.

| Parameter | Sample No. 1 Load: 4.6 to 5.4 g N/m³ per day | Sample No. 2 Load: 5.4 g N/m³ per day | Sample No. 3 Load: 1.5 g N/m³ per day | Calculation method |
|---|---|---|---|---|
| Fats | 24% | 22% | 23% | Chloroform/methanol extraction |
| Carbohydrates | 24% | 25% | ~50%[1] | Total fiber |
| Proteins | 51% | 57% | 24% | Total non-soluble nitrogen × 6.25 |
| Ash | 2.7% | 2.6% | 3%[2] | Combustion at 550° C. without phosphorus |

The carbohydrates were estimated by a subtraction from 100% less the fat, protein, and ash content. Phosphorus was not subtracted from this ash content. The fats consisted of 35% linoleic (omega-3) acid. The carbohydrates consisted primarily of hemicellulose.

TABLE 11

Ratio of the fats, carbohydrates, and protein in the algal consortium, based on the nitrogen loads.

| Ratio | Sample No. 1 Load: 4.6 to 5.4 g N/m³ per day | Sample No. 2 Load: 5.4 g N/m³ per day | Sample No. 3 Load: 1.5 g N/m³ per day |
|---|---|---|---|
| Fats:carbohydrates:proteins | 1:1:2 | 1:1:2.5 | 1:2:1 |

Example 7

Effect of Water Temperature on Growth of the Microalgae

Objectives of the Experiments

As a preliminary step, a series of experiments were conducted in order to evaluate the effects of the temperature on algae growth. During the course of these experiments, the temperature of the system was monitored and its effect on the photon yields was measured.

Methods

A temperature acquisition system (thermocouple) was inserted at the edge of the photobioreactor with a capacity of 3 m² (2,000 L), as shown in FIG. 6 and FIG. 7. The culture inside the reactor was stirred by means of the injection of gas at a flow rate of 18 L/min. for a liquid volume of 1,847 L. Lighting was kept at approximately 60% of solar intensity for a period of 12 hours/day. Agitation, which was based on recirculation, was implemented by means of pumping from the surface, with the aid of a diaphragm pump, with reinjection of the biomass at the bottom (1,000 L/hour). The pH was adjusted to a value within the range from 6.5 to 7.5. The duration of these batch experiments ranged from 84 hours to 120 hours.

The fertilizer that was used was a horticultural fertilizer with a 30-10-10 ($N-P_2O_5-K_2O$) formula. A concentrated stock solution (fertilizer concentration of 33 g/L) was prepared with dechlorinated tap water. The stock solution contained a final concentration of 9.9 g/L of N, 1.4 g/L of P, and 2.7 g/L of K.

Results

Temperature is one of the major factors, second only to light, that affect the metabolism and growth rate of microalgae (Mata et al., 2010). The metabolic rate is usually accelerated by high temperatures (while being usually lethal starting at 35° C.) whereas lower temperatures (<16° C.) can inhibit growth (Kumar et al., 2010).

The optimal temperature varies depending on the microalgae species. Microalgae can usually tolerate temperatures that are as much as 15° C. lower than their optimal temperatures, but have greater difficulty tolerating temperatures that are even just a few degrees higher than their optimal temperatures (Mata et al., 2010).

The optimal temperature also varies according to the provenance of the microalgae. For strains originating in temperate environments, the optimum temperature is within the range from 10 to 27° C., and preferably on the order of 16 to 27° C. Thermophilic microalgae are of particular interest in the area of the biofixation of $CO_2$, because the gas produced by industrial plants and factories can reach high temperatures, thereby reducing the cost of cooling.

On hot days in closed systems, the risk of reaching lethal temperatures is very high, sometimes requiring a cooling system in order to maintain an appropriate temperature (Mata et al., 2010).

Figure 13:
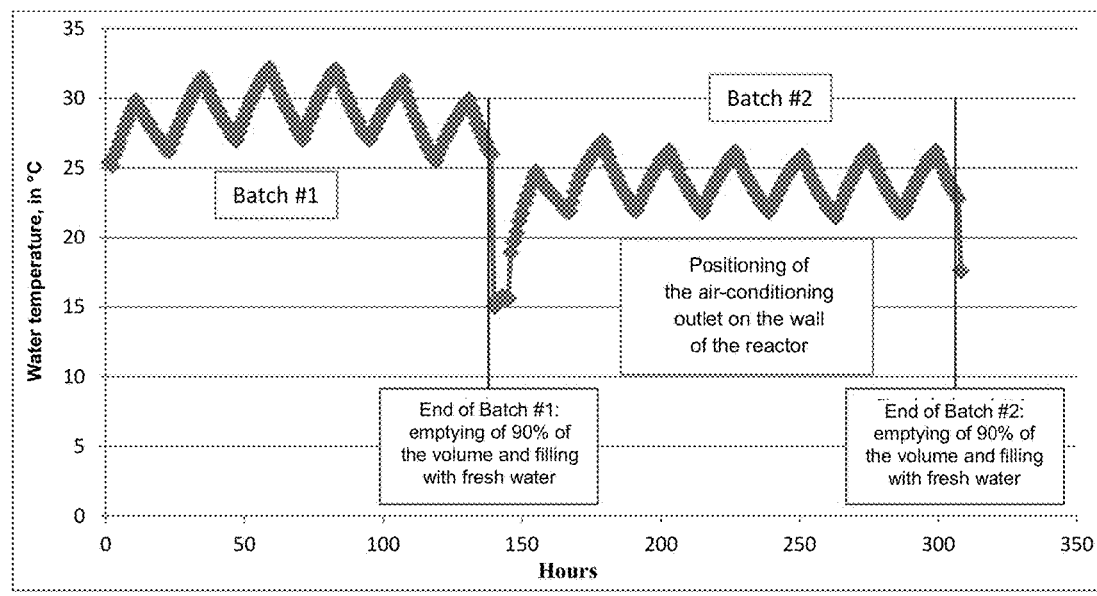
FIG. 13 is a line graph depicting temperature variations for the first two growth vessels in the photobioreactor with a capacity of 3 $m^2$, according to Example 7.

Because of luminous intensity and the heat released by the lamps, a first series of experiments were conducted under temperature conditions equal to or greater than 25° C., and specifically between 25° C. and 32° C. (FIG. 13). The temperature peaks correspond to the illuminated periods, whereas the valleys indicate during the black-out periods. Changes in the position and direction of air-conditioning outlets made it possible to keep the water temperature below 30° C.

Here again, the use of a consortium according to the present invention illustrates the robustness of the culture system. The PY values shown in Table 12 indicate that the algae consortium generates similar growth yields for a system operating within an average temperature range of 24 to 29° C.

TABLE 12

Temperatures for the first two algae culture experiments, and their effect on PY values.

| Mean temp. (° C.) | Min. temp. (° C.) | Max. temp. (° C.) | Number of temperature data points | Final PY value |
|---|---|---|---|---|
| 28.8 | 25.2 | 32.2 | 139 | 32 |
| 24.0 | 21.5 | 26.9 | 145 | 30 |

Example 8

Effect of Water Temperature on Composition of the Microalgae

As a preliminary step, the temperature operating ranges were determined through the use of the thermal simulation for the microalgae culture system. The maximum and minimum temperatures ranges in the reactor were set according to normal temperatures in Quebec city at different period of the year, i.e. at 35° C. to 40° C. (June and July) and at 10 to 15° C. (spring, October, and November). Based on this information, the 20-liter reactors were modified so that an attempt could be made to keep the temperatures within the defined ranges.

For the last batch in each experiment, the fat content and the fatty-acid profile (fatty-acid methyl ester, or FAME), the carbohydrate content, and the protein content were measured, and taxonomic identifications were made, in order to determine the effect of temperature on the biochemical and microbiological composition of the microalgae.

Effect of the Temperature on Growth Performance

The results presented in Table 13 show that there is a twofold photo-yield loss when the system is operating at a higher temperature. Conversely, at low temperatures, the yields are similar to the ones obtained at room temperature. Accordingly, the use of a consortium makes it possible to obtain a procedure that functions over a temperature range from 9° C. to 40° C. Moreover, the trend appears to indicate that the particular consortium tested preferred cold temperatures to hot temperatures.

TABLE 13

Photon yield of the experiments with hot and cold growth temperatures.

| | Photon yield | | |
|---|---|---|---|
| Batch | Room temperature (19 to 23° C.) | 35 to 40° C. | 9 to 12.5° C. |
| 1 | 24.8 | 50.9 | 29.5 |
| 2 | 31.5 | 69.2 | 36.5 |
| 3 | 27.6 | 50.4 | 33.2 |

After the observation of the poor performance of the reactor operating at a hot temperature, additional experiments were performed in order to simulate a return to normal temperatures (i.e., room temperature). The results shown in Table 14 made it possible to validate the robustness of the microalgae consortium in terms of reestablishing itself when hostile conditions are replaced by normal conditions. Accordingly, operation at hot temperatures for more than three weeks did not irreversibly change the yield of the consortium. The performance levels were immediately restored when the temperatures returned to cooler levels.

TABLE 14

Photon yield of the experiments at hot growth temperatures and a return to room temperature.

| | Photon yield | |
|---|---|---|
| Batch | 35 to 40° C. | Return to room temperature (19 to 23° C.) |
| 1 | 50.9 | — |
| 2 | 69.2 | |
| 3 | 50.4 | |
| 4 | — | 32.5 |
| 5 | | 26.5 |

Effect of the Temperature on the Biochemical Characteristics of the Consortium

With regard to the biochemical characteristics of the microalgae consortiums, their composition was evaluated at the end of the series of experiments at different temperatures. The results presented in Table 15 show that there is a certain amount of variation for the fats, the carbohydrates, and the proteins. As can be seen, there appears to be a trend toward an increase in the fat and protein levels when growth occurs at a low temperature. The high protein level may be due to a higher enzyme (protein) level in the algae for the purpose of preserving effective growth metabolism. For information purposes, enzymes are involved in photosynthesis and in all of the processes leading to the production of fats and sugars. Davidson (1991) reported a high level of rubisco enzymes, which are responsible for $CO_2$ fixation when growth occurs in cold water. Nevertheless, the present results demonstrate that the carbohydrate and protein levels can be controlled to a certain extent by the temperature.

TABLE 15

Chemical composition of the microalgae consortium, in relation to the growth temperatures.

| Description | Fats (%) | Carbohydrates (%) | Proteins (%) |
|---|---|---|---|
| Cold temperature (9 to 12.5° C.) | 22.9 | 15.4 | 61.8 |
| Room temperature (19 to 23° C.) | 20.2 | 31.2 | 48.6 |
| Hot temperature (35 to 40° C.) | 20.4 | 28.1 | 51.4 |

The results of the analyses of the fatty-acid profiles of the fat fractions (FAME), as presented in Table 16, show that the consortiums are rich in omega-3 fatty acids. A proportion ranging from 17.0% to 37.4% of these fats in fact consists of omega-3 polyunsaturated fatty acids, and, more specifically, linolenic acid (C18:3). It appears that the omega-3 level is higher when growth takes place at colder temperatures.

TABLE 16

Omega-3 Content of fats extracted from the algae, in relation to the growth temperatures.

| Description | Fats (%) | Omega-3 in the fats (%) | Omega-3 in the microalgae (dry base) (%) |
|---|---|---|---|
| Cold temperature (9 to 12.5° C.) | 22.9 | 37.4 | 8.6 |
| Room temperature (19 to 23° C.) | 20.2 | 29.0 | 5.8 |
| Hot temperature (35 to 40° C.) | 20.4 | 17.0 | 3.5 | the Effect of Temperature on the Microbiological Characteristics of the Consortium Three algae samples were analyzed for identification of the principal species present in the reactors. Table 17 presents the results as a function of the various growth temperatures. The main algal cell morphologies of the consortium are presented in FIG. 15.

TABLE 17

Identification of the principal algae detected during the experiments.

| Reactor | Identification No. 1 | Identification No. 2 | Identification No. 3 |
|---|---|---|---|
| | | Relative proportions | |
| Cold temperature (9 to 12.5° C.) | *Scenedesmus* sp. (dominant) | — | — |
| Room temperature (19 to 23° C.) | *Scenedesmus* sp. 45% | *Scenedesmus acuminatus* 24% | *Scenedesmus acutus* 41% |
| Hot temperature (35 to 40° C.) | *Chlorella* sp. 48% | *Scenedesmus obliquus* 49% | — |

The principal genera that were observed consisted of *Scenedesmus*, primarily for growth conditions at room temperature or colder. For the reactor that operated under hotter conditions, the proportions were divided between the *Chlorella* and *Scenedesmus* genera. These species belong to genera that are often encountered in the natural environment.

Effect of the Temperature on Settling and Adhesion

Figure 14:
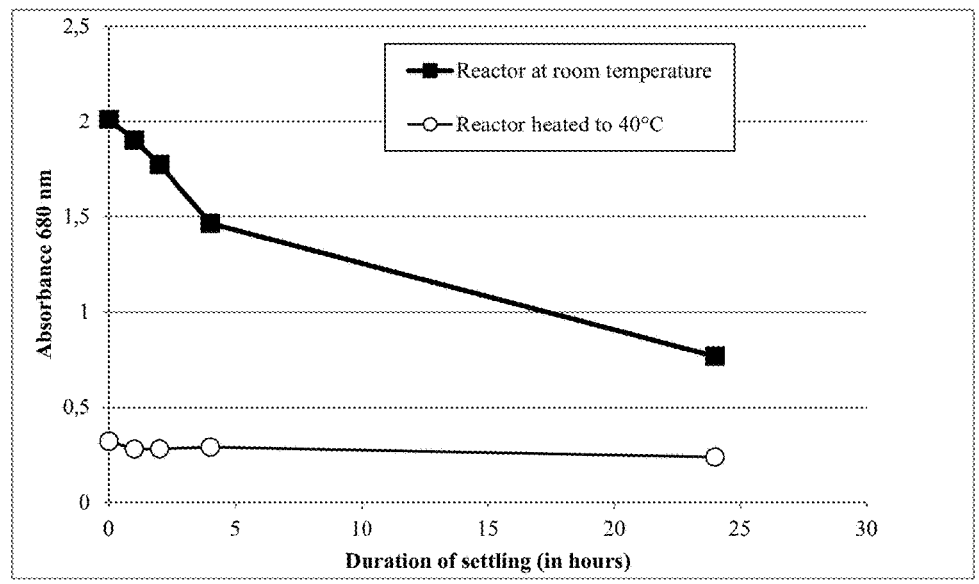
FIG. 14 is a line graph depicting settling for the two reactors that were left to stand, and in which growth took place under different temperature conditions (i.e., room temperature and 40° C.), according to Example 8.

Settling experiments were conducted and a qualitative evaluation of biomass adhesion was performed. In the case described here, the effect of the growth temperature on settling and on adhesion was studied. The settling behavior, as a function of the biomass growth temperature, is shown in FIG. 14.

For the reactor that operated at room temperature, the reduction in absorbance indicates a settling of the material over time. For the reactor that was subjected to higher temperatures, the absorbance value was relatively low, and remained constant throughout the duration of the experiment.

The concentrations of matter in suspension (SS) were measured at the end of the batches, with stirring and $CO_2$ bubbling in accordance with normal operations. This measurement made it possible to determine the quantity of biomass in suspension during the experiment. Next, the interior of the reactors, the optical elements, and all of the immersed structures were rubbed in order to remove the biomass and place it back in suspension. The SS concentrations were measured after this operation. The results for the SS concentrations, before and after the detachment, are shown in Table 18.

TABLE 18

Measurement of the adhesion of the microalgae, in relation to the growth temperatures.

| Reactor | SS before rubbing (mg/L) | SS after rubbing (mg/L) | Adhered biomass (%) |
|---|---|---|---|
| Room temperature (19 to 23° C.) | 600 | 612 | 2 |
| Hot temperature (35 to 40° C.) | 98 | 370 | 78 |

These results made it possible to reach a conclusion regarding the effect of temperature on settling and adhesion. For growth temperatures on the order of 19° C. to 23° C., the algal biomass did not tend to adhere to the surfaces. It also displayed good settling. At hotter growth temperatures the biomass adhered strongly to the surfaces, thereby limiting the amount of biomass in suspension. This low proportion of biomass in suspension also displayed poor settling performance.

Altogether, these results suggest that temperature can be a suitable control means to affect the flocculation and/or settling of the consortium of microalgae and that temperature may also be used to affect adhesion of the microalgae to surfaces of the bioreactor.

Example 9

Effect of the Major Chemical Components of Industrial Flue Gases on Microalgae Growth Objectives of the Experiments The objective of these experiments was to determine the effect of the major chemical components of industrial flue gases on the growth of microalgae consortiums.

Methods

These experiments were conducted in reactors with a capacity of 20 liters that were equipped with stirring devices and a light-diffusion system (pyramidal V-shaped). The selection of the gases contained in the synthetic mixture took into consideration the technical reproduction capabilities and the representative nature of the major constituents of the industrial gases.

The gas that was injected was a synthesized gas that simulated an industrial effluent. It contained carbon monoxide (CO), carbon dioxide ($CO_2$), sulfur dioxide ($SO_2$), nitrogen dioxide ($NO_2$), and carbonyl sulfide (COS) in an air matrix. In order to measure the effect of the gases, the photon yields of the consortium were measured.

A control reactor was monitored in parallel, in order to compare the growth yield of the biomass in contact with the synthetic gas. The control vessel was supplied with a mixture of air and 1% $CO_2$ at a flow rate of 180 mL/min.

Prior to sampling, the gas input was operated at a flow rate of 180 mL/min for a period of three hours, in order to ensure more than 3 changes of air in this area. Because the system was not completely leakproof, the air sampling was done at approximately ¼ of the flow rate of the gaseous flow that was injected into the reactor, in order to eliminate any risk of dilution due to an inflow of external air. A total of 2 liters of gas was sampled, using Flexfoil™ bags and a peristaltic pump.

The CO and the $CO_2$ were analyzed by means of gas-phase chromatography (GC), using equipment that was manufactured by Varian and that contained the following columns: Porapak N™ 0.9 m×⅛" OD×2 mm ID, and Porapak QS™ 1.8 m×⅛" OD×2 mm ID. After elution, the samples were passed through a methanizer, and were then quantified by means of a flame ionization detector (FID). The $SO_2$ and the $NO_2$ were analyzed using an FT-IR device. The COS was not analyzed. The input concentrations were deduced from the analysis certificates for the bottles.

Results

The PY results for the microalgae that were in contact with the synthesized gas (COS, $CO_2$, CO, $SO_2$, and $NO_2$) are shown in Table 19, and are compared against the control that received 1% $CO_2$. The consumption of the synthesized gases was measured during Experiment No. 3, after 5 days of growth.

TABLE 19

Effect of flue gases on microalgae growth in the 20-liter reactor.

| Experiment No. | Growth condition | Final PY value | Duration of the experiment |
|---|---|---|---|
| | Synthesized gas | | |
| 1 | pH between 8.1 and 9.1 gas at 66% of the flow rate | 52 | 7 |
| 2 | pH between 8.7 and 9.7 gas at 100% of the flow rate | 37 | 10 |
| 3 | pH between 7.6 and 8.1 gas at 100% of the flow rate | 38 | 7 |
| | Control | | |
| 1 | 0.18 L/min. air + 1% $CO_2$ | 32 | 7 |
| 2 | 0.18 L/min. air + 1% $CO_2$ | 32 | 10 |
| 3 | 0.18 L/min. air + 1% $CO_2$ | 29 | 7 |

The scientific literature mentions the issues associated with the acidification of the culture due to the injection of gases containing $SO_2$ and $NO_x$ (Hauck et al., 1996; and Lee et al., 2002). In the present case, contrary to expectations, the pH values of the reactor processing the synthesized gases remained essentially basic. The buffering capability of the algae, along with the consumption of the $SO_2$, appeared to prevent any pronounced acidification of the medium. The consortium that was used here appears to be capable of resisting $SO_X$ concentrations that, according to the literature, would normally be inhibitory for certain species (Yanagi et al., 1995; Lee et al., 2002). Furthermore, the study conducted by Lee et al. (2002) on $SO_2$ concentrations on the order of 100 ppm in a pure culture indicated growth inhibition values on the order of 66%. For the consortium that was used here, this productivity loss was much lower (approximately 26%, with an PY value of 37 as opposed to a control PY value of 31) for an $SO_2$ concentration of 130 ppm (Table 19).

The photon yields of the cultures in the presence of the synthesized gas were slightly lower than the yields obtained with the control reactor that received only 1% $CO_2$. For the two batches that followed the implementation, photon yields on the order of 37 and 38 were obtained, in comparison with 28 and 29 for the control. Thus, the adaptation of the biomass must have taken place over a shorter period of time. A longer adaptation period would probably have made it possible to obtain higher yields, along with a biomass that was better adapted to the synthesized gases. Furthermore, other researchers have reported that certain microalgae species have their own individual ability to resist certain concentrations of the various contaminants that are present in flue gases (Sahoo et al., 2012; Ono and Cuella, 2003). Accordingly, prolonged tests under conditions that include synthesized gases or industrial gases should make it possible to eliminate the sensible species from the consortium and to favor the resistant species.

The objective of this experiment was to evaluate the behavior of the culture system for each of the injected gases. The concentrations of the gases at the outlet of a reactor were evaluated in order to estimate the removal rates. The results are shown in Table 20 below.

TABLE 20

Analysis of the gases at the outlet after 7 days of growth.

| Chemical compound | Concentration | | Removal percentage (%) |
|---|---|---|---|
| | Inlet (ppmv) | Outlet (ppmv) | |
| COS | 6 | Not analyzed | — |
| $CO_2$ | 10,000 (1%) | 1,752 | 82.5 |

TABLE 20-continued

Analysis of the gases at the outlet after 7 days of growth.

| Chemical compound | Concentration | | Removal percentage (%) |
|---|---|---|---|
| | Inlet (ppmv) | Outlet (ppmv) | |
| CO | 300 | 271.1 | 9.6 |
| $SO_2$ | 130 | 59.8 | 54.0 |
| $NO_2$ | 7 | Interference | — |

Note that the $NO_2$ concentration at the outlet of the reactor could not be measured, because there was too much infrared interference due to the water vapor, taking into consideration the concentration range that was measured.

The carbon monoxide was not handled by the system to a significant extent. This is not surprising considering that this gas is only sparingly soluble in water, and therefore is largely unavailable to the microorganisms.

Conversely, the $CO_2$ and the $SO_2$ were sequestered in the system at high rates of 82.5% and 54%, respectively. $CO_2$ is the primary source of carbon for growing algae. The processing of the $SO_2$ by the algae is particularly interesting, because $SO_2$ is a pollutant that causes acid rain. Thus, the capture and processing of this pollutant is favorable for the environment.

In summary:

The growth of the consortium was maintained under gas-input conditions that simulated industrial wastes;

The photon yields were slightly lower than the ones that were obtained for a reactor that was supplied solely with 1% $CO_2$;

A longer adaptation period would probably have made it possible to obtain higher yields, along with a biomass that was better adapted to the synthesized gases;

Extended experiments under industrial gas conditions would probably favor resistant species;

Despite the presence of acidifying molecules ($SO_2$), the pH of the cultures remained basic at all times, thereby offering an advantage, in that this condition limits the number of interventions and the addition of expensive reagents to the process; and The bubbling of the gases in the algae growth reactor made it possible to sequester at least 82.5% of the $CO_2$ and 54% of the $SO_2$.

Example 10

Photographs of the Consortium During the Experiments

Samples were taken at the end of the different batches after 7 days of growth in the 2,000-liter system described in Example 3. Photographs of these samples are shown in FIG. 15A-J. These photographs reveals microalgae of at least five (5) different cell morphologies.

REFERENCES

Cadoret J.-P. and Bernard O. (2008). La production de biocarburant lipidique avec des microalgues: promesses et délis. *Journal de la Société de Biologie*, 202 (3), 201-211.

Chinnasamy, S., Bhatnagar, A., Claxton, R., and Das, K. C. (2010). Biomass and bioenergy production potential of microalgae consortium in open and closed bioreactors using untreated carpet industry effluent as growth medium. *Bioresource Technology*, 101 (17), 6751-6760.

Davidson, I. R., Environmental effects on algal photosynthesis temperature, Department of Botany and Plant Pathology and Center for Marine Studies, University of Maine, Journal of Phycology, 27: 2-8,1991

Hauck, J. T., Scierka, S.J., and Perry, M. B. (1996). Effects of simulated flue gas on growth of microalgae. Preprints of papers, *American Chemical Society, Division of Fuel Chemistry*, 41 (CONF-960807).

Jaouen, P., Vandanjon, L., and Quéméneur, F. (1999). The shear stress of microalgal cell suspensions (*Tetraselmis suecica*) in tangential flow filtration systems: The role of pumps. *Bioresource technology*, 68 (2), 149-154.

Kumar, M. S., Miao, Z. H & Wyatt, S. K. (2010). Influence of nutrient loads, feeding frequency and inoculum source on growth of *Chlorella vulgaris* in digested piggery effluent culture medium. *Bioresource technology*, 101(15), 6012-6018.

Lee, J. S., Kim, D. K., Lee, J. P., Park, S. C., Koh, J.H., Cho, H. S., and Kim, S. W. (2002). Effects of SO2 and NO on growth of *Chlorella* sp. KR-1. *Bioresource technology*, 82(1), 1-4.

Li X., Hu Hy, Gan K., Sun Yx, 2012. Effects of different nitrogen and phosphorus concentrations on the growth, nutrient uptake, and lipid accumulation of a freshwater microalgae *Scenedesmus* sp. *Bioresource Technology*, 101 (2010), 5494-5500.

Mata, T. M., Martins, A. A., and Caetano, N. S. (2010). Microalgae for biodiesel production and other applications: A review. *Renewable and Sustainable Energy Reviews*, 14(1), 217-232.

Oilgae Report, Academic Edition (2011), p. 567.

Olguin E. J., Mendoza A. Gonzalez-Portela, R. E. and Novelo E. (2013), New Biotechnology, Volume 30, Issue 6, Sep. 2013, pages 705-715.

Ono, E. and Cuello, J.L. (2003). Selection of optimal microalgae species for CO2sequestration. In *Second National Conference on Carbon Sequestration.[Online]* (Vol. 5, p. 2003).

Sahoo, D., Elangbam, G., and Devi, S. S. (2012). Using algae for carbon dioxide capture and bio-fuel production to combat climate change. *Phykos*, 42 (1), 32-38.

Salim, S., Bosma, R., Vermuë, M. H., and Wijffels, R. H. (2011). Harvesting of microalgae by bio-flocculation. *Journal of Applied Phycology*, 23 (5), 849-855.

Shurin, J. B, Mandal S. and Abbott R. L. (2014), Journal of Applied Ecology, 2014, doi:10.111/1365-2664.12242.

Smith V. H. and Crews T., Algal Research, (2013), htpp://dx.doi.org/10.1016/j.alga1.2013.11.005.

Tam, N. F. Y. and Wong, Y. S. (1996). Effect of ammonia concentrations on growth of *Chlorella vulgaris* and nitrogen removal from media. *Bioresource Technology*, 57 (1), 45-50.

Wilkie, A. C., Edmundson, S. J., and Duncan, J. G. (2011). Indigenous algae for local bioresource production: Phycoprospecting. *Energy for Sustainable Development*, 15 (4), 365-371.

Yanagi, M., Watanabe, Y., and Saiki, H. (1995). CO2 fixation by *Chlorella* sp. HA-1 and its utilization. *Energy Conversion and Management*, 36 (6), 713-716.

Headings are included herein for reference and to aid in locating certain sections. These headings are not intended to limit the scope of the concepts described therein under, and these concepts may have applicability in other sections throughout the entire specification. Thus, the present invention is not intended to be limited to the embodiments shown herein but is to be accorded the widest scope consistent with the principles and novel features disclosed herein.

As used herein and in the appended claims, the singular forms "a", "an", and "the" include plural referents unless the context clearly indicates otherwise.

Unless otherwise indicated, all numbers expressing quantities of ingredients, reaction conditions, concentrations, properties, and so forth used in the specification and claims are to be understood as being modified in all instances by the term "about". At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

It is understood that the examples and embodiments described herein are for illustrative purposes only and that various modifications or changes in light thereof will be suggested to persons skilled in the art.

We claim:

1. A method for the culture of microalgae, comprising:
providing a consortium of at least two living species of microalgae;
culturing under illumination said consortium in a controllable bioreactor and under non-sterile aqueous culture conditions; and
controlling an amount and/or type of nutrients to minimize adhesion of the microalgae to surfaces of the bioreactor without adversely affecting growth of said consortium of microalgae;
wherein controlling the amount and/or type of nutrients consists essentially of providing a combined source of nitrogen-phosphorus-potassium (N—P—K).

2. The method of claim 1, wherein said adhesion is controlled to facilitate and/or promote harvesting of microalga.

3. The method of claim 1, further comprising the step of harvesting sediments or flocks of microalgae.

4. The method of claim 1, further comprising controlling culture conditions for affecting proteins, carbohydrates and/or lipids content of said consortium.

5. The method of claim 1, further comprising regulating mixing of the consortium.

6. The method of claim 5, wherein said mixing comprises a mixing at an aqueous culture speed of about 1 cm/sec to about 10 cm/sec.

7. The method of claim 5, wherein said mixing comprises a gaseous bubbling at a flow rate of about 0.001 to about 0.1 volume of gas per volume of reactor per minute (VVM).

8. The method of claim 1, wherein controlling the amount and/or type of nutrients comprises maintaining in culture a nitrogen concentration between 0.5 mg/L and 5 mg/L.

9. The method of claim 1, further comprising controlling the culture conditions according to a predetermined use of the consortium that is selected from the group consisting of: $CO_2$ biofixation, elimination or capture of undesirable gaseous substances, production of a protein-rich algal biomass, production of a lipid-rich algal biomass, and production of a carbohydrate-rich algal biomass.

10. The method of claim 9, wherein said controlling comprises maintaining the culture conditions at a temperature between about 9° C. and about 12.5° C.

11. The method of claim 10, wherein maintaining said temperature increases a relative content of omega-3 fatty acid of algal biomass.

12. The method of claim 1, further comprising the step of bubbling into the bioreactor a gas comprising one or more of the following gaseous substances: CO, $CO_2$, $SO_2$, $NO_2$, and COS.

13. The method of claim 10, wherein said gas is a gas originating from an industrial effluent.

14. The method of claim 1, further comprising maintaining a minimal microalgae concentration between about 70 mg/l and about 1000 mg/l of culture.

15. The method of claim 1, further comprising maintaining the culture conditions at a temperature between about 9° C. and about 29° C.

16. The method of claim 1, further comprising maintaining the culture conditions at a pH between about 6.5 and about 8.5.

17. The method of claim 1, wherein said consortium comprises indigenous species of microalgae.

18. The method of claim 1, wherein the bioreactor is an outdoor open bioreactor.

19. The method of claim 18, further comprising regulating said illumination of the consortium, and wherein regulating illumination comprises optimizing amount of sunlight exposure and/or sunlight intensity by using a sunlight distribution device.

20. The method of claim 19, wherein regulating illumination further comprises using a mechanical sun-tracking device.

21. The method of claim 19 wherein the sunlight distribution device is partially immersed in the bioreactor.

22. The method of claim 1, further comprising controlling said culture conditions for promoting flocculation and/or settling of said consortium of microalgae.

23. The method of claim 1, wherein controlling the amount and/or type of nutrients to minimize adhesion of the microalgae to surfaces of the bioreactor without adversely affecting growth of said consortium of microalgae consists of providing a combined source of nitrogen-phosphorus-potassium (N—P—K).

24. A method for the culture of microalgae comprising:
providing a consortium of at least two living species of microalgae;
culturing under illumination said consortium in a controllable bioreactor and under non-sterile aqueous culture conditions;
maintaining the culture conditions at a pH between about 6.5 and about 8.5; and
controlling a nitrogen concentration in the culture between 0.5 mg/L and 5 mg/L
to minimize adhesion of the microalgae to surfaces of the bioreactor, without adversely affecting growth of said consortium of microalgae.

25. The method of claim 24, wherein maintaining said nitrogen concentration consists essentially of providing a combined source of nitrogen-phosphorus-potassium (N—P—K).

26. The method of claim 24, further comprising controlling said culture conditions for promoting flocculation and/or settling of said consortium of microalgae.

27. The method of claim 24, wherein maintaining said nitrogen concentration consists of providing a combined source of nitrogen-phosphorus-potassium (N—P—K).

\* \* \* \* \*